US008853379B2

(12) United States Patent
Tangy et al.

(10) Patent No.: US 8,853,379 B2
(45) Date of Patent: Oct. 7, 2014

(54) CHIMERIC POLY PEPTIDES AND THE THERAPEUTIC USE THEREOF AGAINST A FLAVIVIRIDAE INFECTION

(75) Inventors: Frederic Tangy, Les Lilas (FR); Marianne Lucas-Hourani, Paris (FR); Erika Navarro-Sanchez, Montreuil-sous-Bois (FR); Marie-Pascale Frenkiel, Levallois-Perret (FR); Hugues Bedouelle, Paris (FR); Chantal Combredet, Paris (FR); Philippe Despres, La Garenne-Colombes (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 422 days.

(21) Appl. No.: 13/089,705

(22) Filed: Apr. 19, 2011

(65) Prior Publication Data

US 2012/0201825 A1 Aug. 9, 2012

Related U.S. Application Data

(63) Continuation of application No. 11/917,907, filed as application No. PCT/FR2006/001396 on Jun. 20, 2006, now Pat. No. 8,337,857.

(30) Foreign Application Priority Data

Jun. 20, 2005 (CA) ..................................... 2508266

(51) Int. Cl.
| | |
|---|---|
| *C12N 15/62* | (2006.01) |
| *C12N 15/86* | (2006.01) |
| *C07K 14/005* | (2006.01) |
| *C07K 14/08* | (2006.01) |
| *A61K 39/12* | (2006.01) |
| *A61K 39/00* | (2006.01) |

(52) U.S. Cl.
CPC ....... *C07K 14/005* (2013.01); *A61K 2039/5256* (2013.01); *C12N 2770/24122* (2013.01); *C12N 15/86* (2013.01); *C07K 2319/04* (2013.01); *A61K 39/12* (2013.01); *A61K 2039/53* (2013.01); *C12N 2760/18443* (2013.01); *C12N 2770/24134* (2013.01)

USPC .................... 536/23.4; 536/23.72; 435/320.1; 514/3.7

(58) Field of Classification Search
None
See application file for complete search history.

(56) References Cited

U.S. PATENT DOCUMENTS

| | | | | |
|---|---|---|---|---|
| 8,337,857 | B2 | 12/2012 | Tangy et al. | |
| 2005/0002953 | A1 * | 1/2005 | Herold | 424/186.1 |

FOREIGN PATENT DOCUMENTS

| | | | |
|---|---|---|---|
| WO | 01 96376 | | 12/2001 |
| WO | 2004016586 | A2 | 2/2004 |
| WO | 2004 076619 | | 9/2004 |
| WO | 2004112694 | A2 | 12/2004 |
| WO | 2005 111221 | | 11/2005 |

OTHER PUBLICATIONS

Mok et al., The Open Virology Journal 6: Dec. 22, 2012.*
Zuniga et al., Vaccine 25: 2794-2783, 2007.*
Catteau, Adeline et al., "Dengue virus M protein contains a proapoptotic sequence referred to as ApoptoM", Journal of General Virology, vol. 84, pp. 2781-2793, 2003 (XP-002405613).

Catteau, Adeline et al., "Expression of dengue ApoptoM sequence results in disruption of mitochondrial potential and caspase activation", Biochimie, vol. 85, pp. 789-793,2003 (XP-002405614).

Colombage, G. et al., "DNA-Based and alpha virus-Vectored Immunisation with PrM and E Proteins Elicits Long-Lived AT and protective Immunity against the *Flavivirus*, Murray Valley Encephalitis Virus", Virology, vol. 250, pp. 151-163, 1998 (XP004445627).
Fonseca, Benedito A.L. et al., "Recombinant vaccinia viruses co-expression dengue-1 glycoproteins prM and E induce neutralizing antibodies in mice", Vaccine, vol. 12, No. 3, pp. 279-285, 1994 (XP 009018695).
Crill, Wayne D. et al., "Monoclonal Antibodies That Bind to Domain III of Dengue Virus E Glycoprotein Are the Most AV Efficient Blockers of Virus Adsorption to Vero Cells", Journal of Virology, vol. 75, No. 16, pp. 7769-7773, 2001 (XP-002982315).
Despres, Philippe et al., "Live Measles Vaccine Expressing the Secreted Form of the West Nile Virus Envelope AW Glycoprotein Protects against West Nile Virus Encephalitis", Journal of Infectious Diseases, vol. 191, No. 2, pp. 207-214,2005 (XP009074536).

Mota, Javier et al., "Induction of protective antibodies against dengue virus by tetravalent DNA immunization of mice with domain III of the envelope protein", Vaccine, vol. 23, p. 3469-3476, 2005 (XP004852137).

Wang, Songli et al., "PrM- and Cell-Binding Domains of the Dengue Virus E Protein", Journal of Virology, vol. 73, No. 3, AY pp. 2547-2551, 1999 (XP-002405616).

Hermida, Lisset et al., "A recombinant fusion protein containing the domain AZ II I of the dengue-2 envelope protein is immunogenic and protective in o Additional References sheet(s) attached nonhuman primates", Vaccine, vol. 24, pp. 3165-3171,2006 XPOO5344486.

* cited by examiner

*Primary Examiner* — Phuong Huynh

(74) *Attorney, Agent, or Firm* — Law Office of Salvatore Arrigo and Scott Lee, LLP

(57) ABSTRACT

The invention relates to building a chimeric polypeptide used for preventing or treating a Flaviviridae infection. The use of the inventive chimeric polypeptide for producing recombinant viral vectors such as a measles living viral vector is also disclosed.

15 Claims, 29 Drawing Sheets

FIGURE 1 (SEQ ID NO : 1)
(SEQ ID NO : 2)

```
              M   L   L   S   V   P   L   L   G   L   L   G   L   A   V   16
cgt acg ATG CTG CTA TCC GTG CCG TTG CTG CTC GGC CTC CTC GGC CTG GCC GTC  54

A   R   S   K   G   M   S   Y   V   M   C   T   G   S   F   K   L   E   34
        GCC AGA TCT AAA GGG ATG TCA TAT GTG ATG TGC ACA GGC TCA TTT AAG CTA GAG 108

K   E   V   A   E   T   Q   H   G   T   V   L   V   Q   V   K   Y   E   52
        AAG GAA GTG GCT GAG ACC CAG CAT GGG ACT GTC CTA GTG CAG GTT AAA TAC GAA 162

G   T   D   A   P   C   K   I   P   F   S   T   Q   D   E   K   G   V   70
        GGA ACA GAT GCG CCA TGC AAG ATC CCC TTT TCG ACC CAA GAT GAG AAA GGA GTG 216

T   Q   N   G   R   L   I   T   A   N   P   I   V   T   D   K   E   K   88
        ACC CAG AAT GGG AGA TTG ATA ACA GCC AAT CCC ATA GTT ACT GAC AAA GAA AAA 270

P   V   N   I   E   T   E   P   P   F   G   E   S   Y   I   I   V   G   106
        CCA GTC AAC ATT GAG ACA GAA CCA CCT TTT GGT GAG AGC TAC ATC ATA GTA GGG 324

A   G   E   K   A   L   K   L   S   W   F   K   R   *                   119
        GCA GGT GAA AAA GCT TTG AAA CTA AGC TGG TTC AAG CGA tag cgg ccg cta taa 378 gcg cgc                                                                         384
``` ssCRT       aa 1-17
[EDIII]<sub>DV1</sub>   aa 19-121

FIGURE 2 (SEQ ID NO : 3)
(SEQ ID NO: 4)

```
                M   L   L   S   V   P   L   L   L   G   L   L   G   L   A   V    16
    cgt acg   ATG CTG CTA TCC GTG CCG TTG CTG CTC GGC CTC CTC GGC CTG GCC GTC     54

A   R   S   K   G   M   S   Y   V   M   C   T   G   S   F   K   L   E       34
    GCC AGA TCT AAA GGG ATG TCA TAT GTG ATG TGC ACA GGC TCA TTT AAG CTA GAG      108

K   E   V   A   E   T   Q   H   G   T   V   L   V   Q   V   K   Y   E       52
    AAG GAA GTG GCT GAG ACC CAG CAT GGG ACT GTC CTA GTG CAG GTT AAA TAC GAA      162

G   T   D   A   P   C   K   I   P   F   S   T   Q   D   E   K   G   V       70
    GGA ACA GAT GCG CCA TGC AAG ATC CCC TTT TCG ACC CAA GAT GAG AAA GGA GTG      216

T   Q   N   G   R   L   I   T   A   N   P   I   V   T   D   K   E   K       88
    ACC CAG AAT GGG AGA TTG ATA ACA·GCC AAT CCC ATA GTT ACT GAC AAA GAA AAA      270

P   V   N   I   E   T   E   P   P   F   G   E   S   Y   I   I   V   G      106
    CCA GTC AAC ATT GAG ACA GAA CCA CCT TTT GGT GAG AGC TAC ATC ATA GTA GGG      324

A   G   E   K   A   L   K   L   S   W   F   R   R   D   K   R   S   V      124
    GCA GGT GAA AAA GCT TTG AAA CTA AGC TGG TTC CGA CGA GAC AAA CGT TCC GTG      378

A   L   A   P   H   V   G   L   G   L   E   T   R   T   E   T   W   M      142
    GCA CTG GCC CCA CAC GTG GGA CTT GGT CTA GAA ACA AGA ACC GAA ACA TGG ATG      432

S   S   E   G   A   W   K   Q   I   Q   K   V   E   T   W   A   L   R      160
    TCC TCT GAA GGC GCC TGG AAA CAA ATA CAA AAA GTG GAG ACT TGG GCT TTG AGA      486

H   P   *                                                                   170
    CAC CCA tga tag cgg ccg cta taa gcg cgc                                      516
```

```
ssCRT           aa 1-17
[EDIII]_DV1     aa 19-119
[M^1-40]_DV1    aa 125-172
```

FIGURE 3

FIGURE 6 (SEQ ID NO : 5)

```
CGTACGATGCTGCTATCCGTGCCGTTGCTGCTCGGCCTCCTCGGCCTGGC
CGTCGCCAGATCTAAAGGGATGTCATATGTGATGTGCACAGGCTCATTTA
AGCTAGAGAAGGAAGTGGCTGAGACCCAGCATGGGACTGTCCTAGTGCAG
GTTAAATACGAAGGAACAGATGCGCCATGCAAGATCCCCTTTTCGACCCA
AGATGAGAAAGGAGTGACCCAGAATGGGAGATTGATAACAGCCAATCCCA
TAGTTACTGACAAAGAAAAACCAGTCAACATTGAGACAGAACCACCTTTT
GGTGAGAGCTACATCATAGTAGGGGCAGGTGAAAAAGCTTTGAAACTAAG
CTGGTTCCGACGAGACAAACGTTCCGTGGCACTGGCCCCACACGTGGGAC
TTGGTCTAGAAACAAGAACCGAAACATGGATGTCCTCTGAAGGCGCCTGG
AAACAAATACAAAAAGTGGAGACTTGGGCTTTGAGACACCCATGATAGCG
GCCGCTATAAGCGCGC
```

FIGURE 7 (SEQ ID NO : 6)
(SEQ ID NO : 7)

```
  R   T   M   L   L   S   V   P   L   L   L   G   L   L   G   L   A   V    18
CGT ACG ATG CTG CTA TCC GTG CCG TTG CTG CTC GGC CTC CTC GGC CTG GCC GTC    54

A   R   S   K   G   T   T   Y   G   M   C   T   E   K   F   S   F   A    36
GCC AGA TCT AAA GGC ACA ACC TAT GGC ATG TGC ACA GAA AAA TTC TCG TTC GCG   108

K   N   P   A   D   T   G   H   G   T   V   V   I   E   L   S   Y   S    54
AAA AAT CCG GCG GAC ACT GGT CAC GGA ACA GTT GTC ATT GAA CTT TCC TAC TCT   162

G   S   D   G   P   C   K   I   P   I   V   S   V   A   S   L   N   D    72
GGG AGT GAT GGC CCT TGC AAA ATT CCG ATT GTC TCC GTT GCG AGC CTC AAT GAC   216

M   T   P   V   G   R   L   V   T   V   N   P   F   V   A   T   S   S    90
ATG ACC CCC GTC GGG CGG CTG GTG ACA GTG AAC CCC TTC GTC GCG ACT TCC AGC   270

A   N   S   K   V   L   V   E   M   E   P   P   F   G   D   S   Y   I   108
GCC AAC TCA AAG GTG CTA GTC GAG ATG GAA CCC CCC TTC GGA GAC TCC TAC ATC   324

V   V   G   R   G   D   K   Q   I   N   H   H   W   H   K   K   R   S   126
GTA GTT GGA AGG GGA GAC AAG CAG ATC AAC CAC CAT TGG CAC AAA AAG CGA AGC   378

R   R   S   V   S   V   Q   T   H   G   E   S   S   L   V   N   K   K   144
AGG AGA TCC GTG TCG GTC CAA ACA CAT GGG GAG AGT TCA CTA GTG AAT AAA AAA   432

E   A   W   L   D   S   T   K   A   T   R   Y   L   M   K   T   E   N   162
GAG GCT TGG CTG GAT TCA ACG AAA GCC ACA CGA TAC CTC ATG AAA ACT GAG AAC   486

W   I   V   R   N   P   *   *   R   P   L   *   A   R                   176
TGG ATC GTA AGG AAT CCT TGA TAG CGG CCG CTA TAA GCG CGC                   528
```

FIGURE 8 (SEQ ID NO : 8)
(SEQ ID NO : 9)

```
  R   T   M   L   L   S   V   P   L   L   L   G   L   L   G   L   A   V     18
CGT ACG ATG CTG CTA TCC GTG CCG TTG CTC CTC GGC CTC CTC GGC CTG GCC GTC     54

A   R   S   K   G   M   S   Y   V   M   C   T   G   S   F   K   L   E     36
GCC AGA TCT AAA GGG ATG TCA TAT GTG ATG TGC ACA GGC TCA TTT AAG CTA GAG    108

K   E   V   A   E   T   Q   H   G   T   V   L   V   Q   V   K   Y   E     54
AAG GAA GTG GCT GAG ACC CAG CAT GGG ACT GTC CTA GTG CAG GTT AAA TAC GAA    162

G   T   D   A   P   C   K   I   P   F   S   T   Q   D   E   K   G   V     72
GGA ACA GAT GCG CCA TGC AAG ATC CCC TTT TCG ACC CAA GAT GAG AAA GGA GTG    216

T   Q   N   G   R   L   I   T   A   N   P   I   V   T   D   K   E   K     90
ACC CAG AAT GGG AGA TTG ATA ACA GCC AAT CCC ATA GTT ACT GAC AAA GAA AAA    270

P   V   N   I   E   T   E   P   P   F   G   E   S   Y   I   I   V   G    108
CCA GTC AAC ATT GAG ACA GAA CCA CCT TTT GGT GAG AGC TAC ATC ATA GTA GGG    324

A   G   E   K   A   L   K   L   S   W   F   K   K   G   S   S   I   G    126
GCA GGT GAA AAA GCT TTG AAA CTA AGC TGG TTC AAG AAA GGA AGC AGC ATA GGG    378

K   M   F   E   A   T   A   G   G   S   G   K   G   M   S   Y   S        144
AAA ATG TTC GAA GCA ACC GCC GGA GGA TCA GGA GGG AAA GGA ATG TCA TAC TCT    432

M   C   T   G   K   F   K   I   V   K   E   I   A   E   T   Q   H   G    162
ATG TGT ACA GGA AAG TTT AAA ATT GTG AAG GAA ATA GCA GAA ACA CAA CAT GGA    486

T   I   V   I   R   V   Q   Y   E   G   D   G   S   P   C   K   I   P    180
ACA ATA GTT ATC AGA GTA CAA TAT GAA GGG GAC GGC TCT CCA TGT AAG ATC CCT    540

F   E   I   M   D   L   E   K   R   H   V   L   G   R   L   I   T   V    198
TTT GAG ATA ATG GAT TTG GAA AAA AGA CAC GTC TTA GGT CGC CTG ATT ACA GTT    594

N   P   I   V   T   E   K   D   S   P   V   N   I   E   A   E   P   P    216
AAC CCG ATC GTA ACA GAA AAA GAT AGC CCA GTC AAC ATA GAA GCA GAA CCT CCA    648

F   G   D   S   Y   I   I   I   G   V   E   P   G   Q   L   K   L   N    234
TTC GGA GAC AGC TAC ATC ATC ATA GGA GTA GAG CCG GGA CAA TTG AAA CTC AAC    702

W   F   K   K   G   S   S   I   G   Q   M   F   E   T   T   M   S   G    252
TGG TTT AAG AAA GGA AGT TCC ATC GGC CAA ATG TTT GAG ACA ACA ATG AGC GGC    756

R   V   E   T   W   A   L   R   H   P   *   *   A   R                    266
CGC GTG GAG ACT TGG GCT TTG AGA CAC CCA TAG TAA GCG CGC                    798
```

FIGURE 9 (SEQ ID NO : 10)
(SEQ ID NO : 11)

```
      R   T   M   L   L   S   V   P   L   L   L   G   L   L   G   L   A   V      18
     CGT ACG ATG CTG CTA TCC GTG CCG TTG CTG CTC GGC CTC CTC GGC CTG GCC GTC      54

A   R   S   K   G   M   S   Y   A   M   C   L   N   T   F   V   L   K      36
     GCC AGA TCT AAG GGG ATG AGC TAT GCA ATG TGC TTG AAT ACC TTT GTG TTG AAG     108

K   E   V   S   E   T   Q   H   G   T   I   L   I   K   V   E   Y   K      54
     AAA GAA GTC TCC GAA ACG CAG CAT GGG ACA ATA CTC ATT AAG GTT GAG TAC AAA     162

G   E   D   A   P   C   K   I   P   F   S   T   E   D   G   Q   G   K      72
     GGG GAA GAT GCA CCT TGC AAG ATT CCT TTC TCC ACA GAG GAT GGA CAA GGG AAA     216

A   H   N   G   R   L   I   T   A   N   P   V   V   T   K   K   E   E      90
     GCT CAC AAT GGT AGA CTG ATC ACA GCC AAC CCA GTG GTG ACC AAG AAG GAG GAG     270

P   V   N   I   E   A   E   P   P   F   G   E   S   N   I   V   I   G     108
     CCT GTC AAC ATT GAG GCT GAA CCT CCT TTT GGG GAA AGT AAC ATA GTG ATT GGA     324

I   G   D   K   A   L   K   I   N   W   Y   K   K   G   S   S   I   G     126
     ATT GGA GAC AAA GCC TTG AAA ATT AAC TGG TAC AAG AAG GGA AGC TCG ATT GGG     378

K   M   F   E   A   T   A   G   G   S   G   G   K   G   M   S   Y   T     144
     AAG ATG TTC GAG GCC ACT GCC GGT GGT TCT GGT GGT AAG GGA ATG TCA TAC ACG     432

M   C   S   G   K   F   S   I   D   K   E   M   A   E   T   Q   H   G     162
     ATG TGC TCA GGA AAG TTC TCA ATT GAT AAA GAG ATG GCA GAA ACA CAG CAT GGG     486

T   T   V   V   K   V   K   Y   E   G   A   G   A   P   C   K   V   P     180
     ACA ACA GTG GTG AAA GTC AAG TAT GAG GGT GCT GGA GCT CCA TGT AAA GTT CCC     540

I   E   I   R   D   V   N   K   E   K   V   V   G   R   I   I   S   S     198
     ATA GAG ATA AGA GAT GTG AAC AAG GAA AAA GTG GTT GGG CGT ATC ATC TCA TCT     594

T   P   F   A   E   N   T   N   S   V   T   N   I   E   L   E   P   P     216
     ACC CCT TTT GCT GAG AAT ACC AAC AGT GTG ACC AAT ATA GAA TTG GAA CCC CCT     648

F   G   D   S   Y   I   V   I   G   V   G   D   S   A   L   T   L   H     234
     TTT GGG GAT AGC TAC ATA GTA ATA GGT GTA GGA GAC AGT GCA TTA ACA CTC CAT     702

W   F   R   K   G   S   S   I   G   K   M   F   E   S   T   Y   S   G     252
     TGG TTC AGG AAA GGG AGC TCC ATT GGC AAG ATG TTT GAG TCC ACA TAC AGC GGC     756

R   V   E   T   W   A   L   R   H   P   *   *   A   R                     266
     CGC GTG GAG ACT TGG GCT TTG AGA CAC CCA TAG TAA GCG CGC                     798
```

FIGURE 10 (SEQ ID NO : 12)
(SEQ ID NO : 13)

| | | | | | | | | | | | | | | | | | |
|---|---|---|---|---|---|---|---|---|---|---|---|---|---|---|---|---|---|
| R | T | M | L | L | S | V | P | L | L | L | G | L | L | G | L | A | V | 18 |
| CGT | ACG | ATG | CTG | CTA | TCC | GTG | CCG | TTG | CTG | CTC | GGC | CTC | CTC | GGC | CTG | GCC | GTC | 54 |
| A | R | S | K | G | M | S | Y | V | M | C | T | G | S | F | K | L | E | 36 |
| GCC | AGA | TCT | AAA | GGG | ATG | TCA | TAT | GTG | ATG | TGC | ACA | GGC | TCA | TTT | AAG | CTA | GAG | 108 |
| K | E | V | A | E | T | Q | H | G | T | V | L | V | Q | V | K | Y | E | 54 |
| AAG | GAA | GTG | GCT | GAG | ACC | CAG | CAT | GGG | ACT | GTC | CTA | GTG | CAG | GTT | AAA | TAC | GAA | 162 |
| G | T | D | A | P | C | K | I | P | F | S | T | Q | D | E | K | G | V | 72 |
| GGA | ACA | GAT | GCG | CCA | TGC | AAG | ATC | CCC | TTT | TCG | ACC | CAA | GAT | GAG | AAA | GGA | GTG | 216 |
| T | Q | N | G | R | L | I | T | A | N | P | I | V | T | D | K | E | K | 90 |
| ACC | CAG | AAT | GGG | AGA | TTG | ATA | ACA | GCC | AAT | CCC | ATA | GTT | ACT | GAC | AAA | GAA | AAA | 270 |
| P | V | N | I | E | T | E | P | P | F | G | E | S | Y | I | I | V | G | 108 |
| CCA | GTC | AAC | ATT | GAG | ACA | GAA | CCA | CCT | TTT | GGT | GAG | AGC | TAC | ATC | ATA | GTA | GGG | 324 |
| A | G | E | K | A | L | K | L | S | W | F | K | R | G | R | I | E | T | 126 |
| GCA | GGT | GAA | AAA | GCT | TTG | AAA | CTA | AGC | TGG | TTC | AAG | CGC | GGC | CGC | ATT | GAA | ACC | 378 |
| W | I | L | R | H | P | * | * | A | R | | | | | | | | | 136 |
| TGG | ATC | TTG | AGA | CAT | CCA | TAG | TAA | GCG | CGC | | | | | | | | | 408 |

FIGURE 11 (SEQ ID NO : 14)
(SEQ ID NO : 15)

```
  R   T   M   L   L   S   V   P   L   L   L   G   L   L   G   L   A   V    18
CGT ACG ATG CTG CTA TCC GTG CCG TTG CTG CTC GGC CTC CTC GGC CTG GCC GTC    54

A   R   S   K   G   T   T   Y   G   M   C   T   E   K   F   S   F   A    36
GCC AGA TCT AAA GGC ACA ACC TAT GGC ATG TGC ACA GAA AAA TTC TCG TTC GCG   108

K   N   P   A   D   T   G   H   G   T   V   V   I   E   L   S   Y   S    54
AAA AAT CCG GCG GAC ACT GGT CAC GGA ACA GTT GTC ATT GAA CTT TCC TAC TCT   162

G   S   D   G   P   C   K   I   P   I   V   S   V   A   S   L   N   D    72
GGG AGT GAT GGC CCT TGC AAA ATT CCG ATT GTC TCC GTT GCG AGC CTC AAT GAC   216

M   T   P   V   G   R   L   V   T   V   N   P   F   V   A   T   S   S    90
ATG ACC CCC GTC GGG CGG CTG GTG ACA GTG AAC CCC TTC GTC GCG ACT TCC AGC   270

A   N   S   K   V   L   V   E   M   E   P   P   F   G   D   S   Y   I   108
GCC AAC TCA AAG GTG CTA GTC GAG ATG GAA CCC CCC TTC GGA GAC TCC TAC ATC   324

V   V   G   R   G   D   K   Q   I   N   H   H   W   H   K   *   R   P   126
GTA GTT GGA AGG GGA GAC AAG CAG ATC AAC CAC CAT TGG CAC AAA TAG CGG CCG   378

L   *   A   R                                                            130
CTA TAA GCG CGC                                                            390
```

(SEQ ID NO: 16)
(SEQ ID NO: 17)

```
    R   T   M   L   L   S   V   P   L   L   L   G   L   L   G   L   A   V    18
    CGT ACG ATG CTG CTA TCC GTG CCG TTG CTG CTC GGC CTC CTC GGC CTG GCC GTC    54

A   R   S   K   G   M   S   Y   V   M   C   T   G   S   F   K   L   E    36
    GCC AGA TCT AAA GGG ATG TCA TAT GTG ATG TGC ACA GGC TCA TTT AAG CTA GAG   108

K   E   V   A   E   T   Q   H   G   T   V   L   V   Q   V   K   Y   E    54
    AAG GAA GTG GCT GAG ACC CAG CAT GGG ACT GTC CTA GTG CAG GTT AAA TAC GAA   162

G   T   D   A   P   C   K   I   P   F   S   T   Q   D   E   K   G   V    72
    GGA ACA GAT GCG CCA TGC AAG ATC CCC TTT TCG ACC CAA GAT GAG AAA GGA GTG   216

T   Q   N   G   R   L   I   T   A   N   P   I   V   T   D   K   E   K    90
    ACC CAG AAT GGG AGA TTG ATA ACA GCC AAT CCC ATA GTT ACT GAC AAA GAA AAA   270

P   V   N   I   E   T   E   P   P   F   G   E   S   Y   I   I   V   G   108
    CCA GTC AAC ATT GAG ACA GAA CCA CCT TTT GGT GAG AGC TAC ATC ATA GTA GGG   324

A   G   E   K   A   L   K   L   S   W   F   K   K   G   S   S   I   G   126
    GCA GGT GAA AAA GCT TTG AAA CTA AGC TGG TTC AAG AAA GGA AGC AGC ATA GGG   378

K   M   F   E   A   T   A   G   G   S   G   G   K   G   M   S   Y   S   144
    AAA ATG TTC GAA GCA ACC GCC GGA GGA TCA GGA GGG AAA GGA ATG TCA TAC TCT   432

M   C   T   G   K   F   K   I   V   K   E   I   A   E   T   Q   H   G   162
    ATG TGT ACA GGA AAG TTT AAA ATT GTG AAG GAA ATA GCA GAA ACA CAA CAT GGA   486

T   I   V   I   R   V   Q   Y   E   G   D   G   S   P   C   K   I   P   180
    ACA ATA GTT ATC AGA GTA CAA TAT GAA GGG GAC GGC TCT CCA TGT AAG ATC CCT   540

F   E   I   M   D   L   E   K   R   H   V   L   G   R   L   I   T   V   198
    TTT GAG ATA ATG GAT TTG GAA AAA AGA CAC GTC TTA GGT CGC CTG ATT ACA GTT   594

N   P   I   V   T   E   K   D   S   P   V   N   I   E   A   E   P   P   216
    AAC CCG ATC GTA ACA GAA AAA GAT AGC CCA GTC AAC ATA GAA GCA GAA CCT CCA   648

F   G   D   S   Y   I   I   I   G   V   E   P   G   Q   L   K   L   N   234
    TTC GGA GAC AGC TAC ATC ATC ATA GGA GTA GAG CCG GGA CAA TTG AAA CTC AAC   702

W   F   K   K   G   S   S   I   G   Q   M   F   E   T   T   M   G   G   252
    TGG TTT AAG AAA GGA AGT TCC ATC GGC CAA ATG TTT GAG ACA ACA ATG GGA GGA   756

S   K   G   M   S   Y   A   M   C   L   N   T   F   V   L   K   K   E   270
    TCT AAG GGG ATG AGC TAT GCA ATG TGC TTG AAT ACC TTT GTG TTG AAG AAA GAA   810

V   S   E   T   Q   H   G   T   I   L   I   K   V   E   Y   K   G   E   288
    GTC TCC GAA ACG CAG CAT GGG ACA ATA CTC ATT AAG GTT GAG TAC AAA GGG GAA   864

D   A   P   C   K   I   P   F   S   T   E   D   G   Q   G   K   A   H   306
    GAT GCA CCT TGC AAG ATT CCT TTC TCC ACA GAG GAT GGA CAA GGG AAA GCT CAC   918
```

*FIG. 12A*

(SEQ ID NO: 16)
(SEQ ID NO: 17)

```
      N   G   R   L   I   T   A   N   P   V   V   T   K   K   E   E   P   V       324
     AAT GGT AGA CTG ATC ACA GCC AAC CCA GTG GTG ACC AAG AAG GAG GAG CCT GTC       972

N   I   E   A   E   P   P   F   G   E   S   N   I   V   I   G   I   G       342
     AAC ATT GAG GCT GAA CCT CCT TTT GGG GAA AGT AAC ATA GTG ATT GGA ATT GGA      1026

D   K   A   L   K   I   N   W   Y   K   K   G   S   S   I   G   K   M       360
     GAC AAA GCC TTG AAA ATT AAC TGG TAC AAG AAG GGA AGC TCG ATT GGG AAG ATG      1080

F   E   A   T   A   G   G   S   G   G   K   G   M   S   Y   T   M   C       378
     TTC GAG GCC ACT GCC GGT GGT TCT GGT GGT AAG GGA ATG TCA TAC ACG ATG TGC      1134

S   G   K   F   S   I   D   K   E   M   A   E   T   Q   H   G   T   T       396
     TCA GGA AAG TTC TCA ATT GAT AAA GAG ATG GCA GAA ACA CAG CAT GGG ACA ACA      1188

V   V   K   V   K   Y   E   G   A   G   A   P   C   K   V   P   I   E       414
     GTG GTG AAA GTC AAG TAT GAG GGT GCT GGA GCT CCA TGT AAA GTT CCC ATA GAG      1242

I   R   D   V   N   K   E   K   V   V   G   R   I   I   S   S   T   P       432
     ATA AGA GAT GTG AAC AAG GAA AAA GTG GTT GGG CGT ATC ATC TCA TCT ACC CCT      1296

F   A   E   N   T   N   S   V   T   N   I   E   L   E   P   P   F   G       450
     TTT GCT GAG AAT ACC AAC AGT GTG ACC AAT ATA GAA TTG GAA CCC CCT TTT GGG      1350

D   S   Y   I   V   I   G   V   G   D   S   A   L   T   L   H   W   F       468
     GAT AGC TAC ATA GTA ATA GGT GTA GGA GAC AGT GCA TTA ACA CTC CAT TGG TTC      1404

R   K   G   S   S   I   G   K   M   F   E   S   T   Y   S   G   R   V       486
     AGG AAA GGG AGC TCC ATT GGC AAG ATG TTT GAG TCC ACA TAC AGC GGC CGC GTG      1458

E   T   W   A   L   R   H   P   *   *   A   R                               498
     GAG ACT TGG GCT TTG AGA CAC CCA TAG TAA GCG CGC                              1494
```

FIG. 12B

FIGURE 13 (SEQ ID NO : 18)

CGTACGATGCTGCTATCCGTGCCGTTGCTGCTCGGCCTCCTCGGCCTGGC
CGTCGCCAGATCTAAGGGAACAACCTATGGCGTCTGTTCAAAGGCTTTCA
AGTTTCTTGGGACTCCCGCAGACACAGGTCACGGCACTGTGGTGTTGGAA
TTGCAGTACACTGGCACGGATGGACCTTGCAAAGTTCCTATCTCGTCAGT
GGCTTCATTGAACGACCTAACGCCAGTGGGCAGATTGGTCACTGTCAACC
CTTTTGTTTCAGTGGCCACGGCCAACGCTAAGGTCCTGATTGAATTGGAA
CCACCCTTTGGAGACTCATACATAGTGGTGGGCAGAGGAGAACAACAGAT
TAATCACCATTGGCACAAGTAGCGGCCGCTATAAGCGCGC

FIGURE 14 (SEQ ID NO : 19)

CGTACGATGCTGCTATCCGTGCCGTTGCTGCTCGGCCTCCTCGGCCTGGC
CGTCGCCAGATCTAAGGGAACAACCTATGGCGTCTGTTCAAAGGCTTTCA
AGTTTCTTGGGACTCCCGCAGACACAGGTCACGGCACTGTGGTGTTGGAA
TTGCAGTACACTGGCACGGATGGACCTTGCAAAGTTCCTATCTCGTCAGT
GGCTTCATTGAACGACCTAACGCCAGTGGGCAGATTGGTCACTGTCAACC
CTTTTGTTTCAGTGGCCACGGCCAACGCTAAGGTCCTGATTGAATTGGAA
CCACCCTTTGGAGACTCATACATAGTGGTGGGCAGAGGAGAACAACAGAT
TAATCACCATTGGCACAAGAGACGCAGTCGGAGGTCACTGACAGTGCAGA
CACACGGAGAAAGCACTCTAGCGAACAAGAAGGGGCTTGGATGGACAGC
ACCAAGGCCACAAGGTATTTGGTAAAAACAGAATCATGGATCTTGAGGAA
CCCTTGATAGCGGCCGCTATAAGCGCGC

FIGURE 15 (SEQ ID NO : 20)

```
MLLSVFLLLG LLCLAVADKL TLKGMSYVMC TGSFKLEKEV ABTQHGTVLV QVKYEGTDAP    60
CKIPFSTQDE KGVTQNGRLI TANPIVTDKE KPVNIETEPP FGESYIIVGA GEKALKLSWF   120
RRCKRSVALA PHVGLGLETR TETWMSSEGA WKQIQKVETW ALRHPRRDKR DKLQLKGMSY   180
SMCTGKFKIV KEIAETQHGT IVIRVQYEGD GSFCKIPFEI TDLEKRHVLG RLITVNPIVT   240
ENDSPVNIEA EPPFGESYII VGVEPGQLKL NWFRRDKRSV ALAPHVGLGL ETRTETWMSS   300
EGAWKQIQKV ETWALRHPRR DKRDKLKLKG MSYAMCLNTF VLKKEVSETQ HGTILIKVEY   360
KGEDAPCKIP FSTEDGQSKA HNGRLITANP VVTKKEEPVN IEAEPPFGES NIVTGIGDKA   420
LKINWYRRDK RSVALAPHVG LGLETRTETW MSSEGAWKQI QKVETWALRH PRRDKREKLR   480
IKGMSYTMCS GKFSIDKEMA ETQHGTTVVK VKYEGAGAPC KVPIEIRDVN KEKVVGRIIS   540
STPLAENTNS VCNIELEPPF GDSYIVIGVG NSALTLHWFR RDKRSVALAP HVGLGLETRT   600
ETWMSSEGAW KQIQKVETWA LRHP                                          624
```

Signal peptide:          aa 1 to 17

DV1 EDIII:               aa 18 to 120
DV2 EDIII:               aa 171 to 273
DV3 EDIII:               aa 324 to 426
DV4 EDIII:               aa 477 to 579 ectoM DV1:               aa 126 to 165
                         aa 279 to 318
                         aa 432 to 471
                         aa 585 to 624 binding segment:         aa 121 to 125
                         aa 166 to 170
                         aa 274 to 278
                         aa 319 to 323
                         aa 427 to 431
                         aa 472 to 476
                         aa 580 to 584

FIGURE 16 (SEQ ID NO : 21)

```
MLLSVFLLLG LLGLAVADKL TLKGMSYVMC TGSFKLEKEV AETQHGTVLV QVKYEGTDAP    60
CKIPFSTQDE KGVIQNGRLI TANPIVTDKE KPVNIETEPP FGESYIIVGA GEKALKLSWF   120
SVALAPHVSI GLETRTETWM SSEGAWKQIQ KVETWALRHP RRDKRDKLQL KGMSYSMCTG   180
KFKIVKEIAE TQHGTIVIRV QYEGDGSPCK IPFEITDLEK RHVLGRLITV NPIVTEKDSP   240
VNIEAEPPFG DSYIIVGVEP GQLKLNWFSV ALAPHVGLGL ETRTETWMSS EGAWKQIQKV   300
ETWALRHPRR DKRDKLKLKG MSYAMCLNTF VLKKEVSETQ HGTILIKVEY KGEDAPCKIP   360
FSTEDGQGKA HNGRLITANP VVTKKEEPVN IEAEPPFGKS KVIGIGDKA LKINWYSVAL   420
APHVGLGLET RTETWMSSEG AWKQIQKVET WALRHPRRDK REKLRIKGMS YTMCSGKFSI   480
DKEMAETQHG TTVVKVKYEG AGAPCKVPIE IRDVNKEKVV GRIISSTPLA ENTNSVTNIE   540
LEPPFGDSYI VIGVGNSALT LHWFRRDKRS VALAPHVGLG LETRTETWMS SEGAWKQICK   600
VETWALRHP                                                           609
```

| | |
|---|---|
| Signal peptide: | aa 1 to 17 |
| DV1 EDIII: | aa 18 to 120 |
| DV2 EDIII: | aa 166 to 268 |
| DV3 EDIII: | aa 314 to 416 |
| DV4 EDIII: | aa 462 to 563 |
| ectoM DV1: | aa 121 to 160 |
| | aa 269 to 308 |
| | aa 417 to 456 |
| | aa 570 to 609 |
| binding segment: | aa 161 to 165 |
| | aa 309 to 313 |
| | aa 457 to 461 |
| | aa 564 to 569 |

FIGURE 17 (SEQ ID NO : 22)

```
MLLSVPLLLG LLGLAVADKL TLKGMSYVMC TGSFKLEKEV AETQHGTVLV QVKYEGTDAP    60
CKIPFSTQDE KGVTQNGRLI TANPIVTDKE KPVNIETEPP FGESYIIVGA GEKALKLSWF   120
RRCKRSVALA PHVGLGLETR TETWMSSEGA WKQIQKVETW ALRHPRRDKR DKLQLKGMSY   180
SMCTGKFKIV KEIAETQHGT IVIRVQYEGD GSPCKIPFEI TDLEKRHVLG RLITVNPIVT   240
EKDSPVNIEA EPPFGDSYII VGVEPGQLKL NWFRREKRSV ALVPHVGMGL ETRTETWMSS   300
EGAWKHVQRI ETWILRHPRR DKRDKLKLKG MSYAMCLNTF VLKKEVSETQ HGTILIKVEY   360
KGEDAPCKIP FSTEDGQGKA HNGRLITANP VVTKKEEPVN IEAEPPFGES NIVIGIGDKA   420
LKINWYRRDK RSVALAPHVG MGLDTRTQTW MSAEGAWRQV EKVETWALRH PRRDKREKLR   480
IKGMSYTMCS GKFSIDKEMA ETQHGTTVVK VKYEGAGAPC KVPIEIRDVN KEKVVGRIIS   540
STPLAENTNS VTNIEIEPPF GDSYIVIGVG NSALTLHWFR REKRSVALTP HSGMGLETRA   600
ETWMSSEGAW KHAQRVESWI LRNP                                         624
```

Signal peptide:            aa 1 to 17

DV1 EDIII:                 aa 18 to 120
DV2 EDIII:                 aa 171 to 273
DV3 EDIII:                 aa 324 to 426
DV4 EDIII:                 aa 477 to 579 ectoM DV1:                 aa 126 to 165
ectoM DV2:                 aa 279 to 318
ectoM DV3:                 aa 432 to 471
ectoM DV4:                 aa 585 to 624 binding segment:           aa 121 to 125
                           aa 166 to 170
                           aa 274 to 278
                           aa 319 to 323
                           aa 427 to 431
                           aa 472 to 476
                           aa 580 to 584

FIGURE 18 (SEQ ID NO : 23)

```
MLLSVPLLLG LLGLAVADKL TLKGMSYVMC TGSFKLEKEV AETQHGTVLV QVKYEGTDAP    60
CKIPFSTQDE KGVTQNGRLI TANPIVTDKE KPVNIETEPP FGESYIIVGA GEKALKLSWF   120
RRDKRDKLQL KGMSYSMCTG KFKIVKEIAE TQHGTIVIRV QYEGDGSPCK IPFEITDLEK   180
KHVLGRLITV NPIVTEKDSP VKIEASPPFG DSYIIVGVEP GQLKLNWFRR CKRDKLKLKG   240
MSYAMCLNTF VLKKEVSETQ HGTILIKVEY KGEDAPCKIP FSTEDGQGKA HNGRLITANP   300
VVTKKEEPVN IEAEPPFGES NIVIGIGDKA LKINWYRRDK REKLRIKGMS YTMCSGKFSI   360
DKEMAETQHG TTVVKVKYEG AGAPCKVPIE IRDVNKEKVV GRIISSTPLA ENTNSVTNIE   420
LEPPFGDSYI VIGVGNSALT LHWFRRDKRS VALAPHVGLG LETRTETWMS SEGAWKQICK   480
VETWALRHP                                                          489
```

Signal peptide:            aa 1 to 17

DV1 EDIII:                aa 18 to 120
DV2 EDIII:                aa 126 to 228
DV3 EDIII:                aa 234 to 336
DV4 EDIII:                aa 342 to 444 ectoM DV1:                aa 450 to 489 binding segment:       aa 121 to 125
                               aa 229 to 233
                               aa 337 to 341
                               aa 445 to 449

FIGURE 19 (SEQ ID NO : 24)

```
MLLSVPLLLG LLGLAVADKL TLKGMSYVMC TGSFKLEKEV AETQHGTVLV QVKYEGTDAP    60
CKIPFSTQDE KGVTQNGRLI TANPIVTDKE KPVNIETEPP FGESYIIVGA GEKALKLSWF   120
DKLQLKGMSY SMCTGKFKIV KEIAETQHGT IVIRVQYEGD GSPCKIPFEI TDLEKRHVLG   180
RLITVNPIVT EKDSPVNIEA EPPFGDSYII VGVEPGQLKL NWFDKLRLKG MSYAMCLNTF   240
VLKKEVSETQ HGTILIKVEY KGEDAPCKIP FSTEDGQGKA HNGRLITANP VVTKKEEPVN   300
IEAEPPFGES NIVIGIGDKA LKINWYEKLR IKGMSYTMCS GKFSIDKEMA ETQHGTTVVK   360
VKYEGAGAPC KVPIEIRDVN KEKVVGRIIS STPLAENTNS VTNIELEPPF GDSYIVIGVG   420
HSALTLHWFR KDKRSVALAP HVGLGLETRT ETWMSSEGAW KQIQKVETWA LRHP          474
```

| | |
|---|---|
| Peptide signal: | aa 1 to 17 |
| DV1 EDIII: | aa 18 to 120 |
| DV2 EDIII: | aa 121 to 223 |
| DV3 EDIII: | aa 224 to 326 |
| DV4 EDIII: | aa 327 to 429 |
| ectoM DV1: | aa 435 to 474 |
| binding segment: | aa 430 to 434 |

FIGURE 20 (SEQ ID NO : 25)

```
cgtacgatgc tcctttccgt cccgttgcta ttaggactac tcgggttggc tgtcgccgat      60
aagctgactc tgaagggaat gtcatacgtt atgtgcacag ggagcttcaa gttggagaag     120
gaggtggcag agacccagca cggaacagtc ttggtgcagg tcaagtacga gggcacggac     180
gctccttgta agatcccatt ctcaacccag gatgagaagg gcgtgaccca gaatggacgg     240
ctgatcacgg ctaatcccat cgtgactgat aaggagaagc cagtcaacat cgagacagag     300
ccaccottcg gtgagtctta cataatagtc ggggccggag agaaggctct caagctgagt     360
tggttcaggc gggataagcg aagcgtcgca cttgccccac acgttggcct cggactcgag     420
acaagaacag agacctggat gagcagcgag ggagcctgga agcagattca gaaggttgag     480
acctgggctc tccggcaccc tcgccgtgat aagagagaca agctgcagct taaggggatg     540
agttattcca tgtgcacagg caagttcaag attgtcaagg agatagcaga gactcagcac     600
ggaaccatag tgatcagagt tcagtacgag ggagacggat ccccatgcaa gattccgttt     660
gagattaccg acctggagaa gcgccacgtg ctggggagac tcattactgt gaacccaatc     720
gtgactgaga aggattctcc cgtcaatatc gaggctgagc caccattcgg agattcttat     780
ataatcgttg gtgtagagcc tggccagttg aagttgaatt ggtttaggcg ggataagagg     840
agcgtggctc tcgctccaca tgttggcctg ggcctggaga cccgaacaga gacgtggatg     900
agctccgaag gtgcctggaa gcagattcag aaggttgaga cctgggccct gcgacaccct     960
agacgggata agcgcgataa gctgaagctt aagggtatgt cctacgcaat gtgcctgaac    1020
acgttcgtgc tgaagaagga ggtttcagag acccagcacg ggacaattct cattaaggtg    1080
gagtacaagg gcgaggacgc gccctgcaag atcccgttca gtactgaaga tggacagggc    1140
aaggctcaca atgggcgact cattactgct aatccagtgg tgaccaagaa ggaagagcca    1200
gtgaatatag aggcagagcc accatttgga gagagcaaca tcgtgatagg tatcggcgat    1260
aaggcactga agatcaactg gtatcgccgc gacaagcgat ccgtggcatt ggcgcctcat    1320
gtgggcctgg gtctagagac ccgcacagag acgtggatga gtagcgaagg cgcgtggaag    1380
cagatccaga aggtcgagac ttgggcactg cggcaccctc gacgtgacaa gcgagagaag    1440
ctccgaatca agggaatgag ttacacaatg tgcagcggca agttctcaat tgataaggag    1500
atggccgaga cccagcacgg cacaaccgtg gtcaaggtca agtacgaagg tgcgggcgct    1560
ccttgcaagg tcccaatcga gattagggat gtgaacaagg agaaggtcgt gggaagaatc    1620
attagttcca cgcctcttgc tgagaacact aatagtgtca ccaatatcga gctagagcca    1680
cccttcggag attcttacat tgtcattgga gttggcaatt ccgctcttac tctgcattgg    1740
tttaggagag ataagagaag cgtggccctg gcaccacacg tgggattagg ctggagaca     1800
cgaaccgaga cctggatgag cagcgaagga gcctggaagc agattcagaa ggtcgagact    1860
tgggccctca gacacccttg atgagcgcgc                                     1890
```

FIGURE 21 (SEQ ID NO : 26)

```
cgtacgatgc tgttgagcgt gccattattg ctggggctgc tgggtctggc tgtggccgac      60
aagcttaccc tgaagggtat gagctacgtg atgtgcactg gttcgttcaa gctagagaag     120
gaggtggcag agacccagca tggaactgtg ttagtacaag ttaagtatga ggggaccgac     180
gcaccctgta agattccatt ctctacccaa gacgagaagg gcgtcacgca gaatggtcgc     240
ttgattacgg ctaatccaat agtgacggac aaggagaagc cagtgaatat cgagacagaa     300
cctccatttg gagaatccta cataatagtc ggggccggcg agaaggccct gaagttgtcc     360
tggttcagcg tggccctggc tccacacgtg ggcctgggcc tggagacccg aactgagact     420
tggatgtcgt ccgagggcgc ctggaagcag atccagaagg tagagacttg ggccctgcgc     480
catcctagga gagataagag ggacaagttg cagctcaagg gcatgtccta ctccatgtgt     540
acaggtaagt tcaagattgt gaaggagatt gctgagaccc agcacggcac catcgtaata     600
cgggtgcagt acgagggcga tggcagtcca tgtaagatac ctttcgagat cactgacctt     660
gagaagcgcc acgtgcttgg gcggctcatt accgtcaatc caatcgtgac tgagaaggat     720
agtccggtga atattgaggc tgagccgccg tttggggata gttatataat cgttggcgtg     780
gagcccggac aactcaagtt gaattggttc tctgtggcct tggcaccaca cgtggggctg     840
ggcctggaga cacggaccga gacttggatg tcaagtgaag gagcctggaa gcagattcag     900
aaggtggaga cttgggccct tcggcaccct agacgtgata agcgcgacaa gctgaagctc     960
aagggaatgt cttacgccat gtgtctgaat actttcgtcc tgaagaagga ggtgtccgag    1020
actcagcatg ggactatcct gatcaaggtg gagtacaagg gtgaagacgc accatgtaag    1080
ataccattca gcacagagga cggtcagggc aaggctcata acgggcgcct tataactgcc    1140
aatccggttg tgaccaagaa ggaggagccc gtgaacatcg aggcagagcc accattcggc    1200
gagtccaaca tcgtgatagg aatcggtgat aaggccctca agattaattg gtattcagtg    1260
gccctggccc ctcacgtcgg actgggactc gagaccagga cagagacatg gatgtcttct    1320
gagggtgcat ggaagcagat acagaaggtt gagacctggg ccctcaggca cccacgtagg    1380
gacaagcggg agaagttgag gattaagggg atgtcgtaca ccatgtgcag cggcaagttc    1440
tccattgaca aggagatggc agagacgcag cacggaacaa cggtcgttaa ggtcaagtac    1500
gaaggagcgg gcgcccatg caaggtccca atcgagatta gggacgtgaa caaggagaag    1560
gttgtaggac ggattattag tagcaccca ctggcggaga atacgaatag tgtcacgaat    1620
atcgaactgg aaccacctt cggcgatagc tacatcgtga ttggtgttgg caattccgca    1680
cttacactgc actggtttcg gagagacaag cgaagcgtgg ccctggcccc tcacgtggga    1740
cttggcctgg agaccccgcac agagacttgg atgtcctctg aaggagcatg gaagcagatt    1800
cagaaggtgg agacttgggc attacgccac ccatgagcgc gc                       1842
```

FIGURE 22 (SEQ ID NO : 27)

```
cgtacgatgc tgctatctgt gccactgctc ctgggactgc tggggctggc cgtggctgac    60
aagttgacgc ttaaggggat gtcctacgta atgtgcacag gatcattcaa gctagagaag   120
gaagttgcag agacgcagca cggcaccgtg ctggttcagg tgaagtacga gggcactgat   180
gcaccctgca agatcccatt cagtactcag gacgagaagg gagtcacgca gaatgggagg   240
ctcatcacgg ccaacccaat tgttaccgac aaggagaagc ccgttaatat agagactgaa   300
ccgcccttcg gggagtcata cattattgtg ggcgcagggg agaaggctct gaagctttcc   360
tggttccgta gggataagcg cagcgtggcg ctagcccctc atgtgggtct cgggctggag   420
actcgcaccg agacatggat gtcatccgag ggtgcgtgga agcagatcca gaaggttgag   480
acatgggcac ttcgccaccc acggcgcgac aagcgtgaca agcttcagct gaaggggatg   540
tcttatagca tgtgcacagg caagttcaag atcgtcaagg agatagcaga gacacagcat   600
ggcacaatag tcatacgggt gcaatatgag ggagatggct ctccgtgtaa gataccttc    660
gagatcaccg atctggagaa gcggcacgtc ctcgggagac taattacggt gaacccaatt   720
gtgacagaga aggatagccc agttaatatt gaggccgaac caccttcgg agacagctac    780
attatcgtag gagtcgagcc agggcagctg aagctgaact ggttccgcag ggagaagcgt   840
tccgtcgctc ttgttccaca tgtgggaatg ggcctggaaa cccgcaccga gacatggatg   900
agcagcgagg gtgcctggaa gcacgtacag agaattgaga cttggatctt aaggcatcct   960
cggcgggata agcgcgacaa gttgaagctg aagggaatgt cttacgcaat gtgtttgaac  1020
actttcgtcc tgaagaagga ggtgtcagag acccagcacg gaactatact tattaaggtt  1080
gagtacaagg gagaagacgc tccttgcaag atcccattct caactgaaga tgggcagggc  1140
aaggcacaca acggaaggct catcacagct aacccagtgg ttaccaagaa ggaggagccc  1200
gtgaacatcg aagccgagcc gcccttcgga gagacaaca tagtgatcgg tattggggat    1260
aaggctctga agatcaattg gtatcgccgg gacaagagaa gtgtggccct ggccccacat  1320
gtcggcatgg gcttggacac acggacacag acatggatgt ccgctgaagg agcctggagg  1380
caggtggaga aggtcgagac ctgggcgctg cgccacccgc gtcgagacaa gagagagaag  1440
ttaagaatca agggtatgtc ctacacgatg tgttccggta agttctccat agacaaggag  1500
atggctgaga cccagcacgg cactacggtg gtcaaggtga agtatgaggg agccggcgca  1560
ccttgcaagg tgccgatcga gatccgcgac gtcaacaagg agaaggtggt cgggcgcatc  1620
atttccagta ccccattagc tgagaatact aatagcgtga ctaatattga gttggaacca  1680
ccttcggag actcttacat cgttatcggg gtgggcaact cagctcttac acttcactgg   1740
ttccgcaggg agaagagatc agtggcccta accctcact caggcatggg cctggagact  1800
cgggccgaga cctggatgag cagcgagggt gcctggaagc acgcccagcg agtggaatcg  1860
tggattctta ggaatccatg atgagcgcgc                                    1890
```

FIGURE 23 (SEQ ID NO : 28)

```
cgtacgatgc tgttatctgt acctctcctg ctcggcctcc ttggactggc agttgcagat      60
aagcttacac tcaagggaat gtcctatgtg atgtgtaccg ggtccttcaa gttggagaag     120
gaggtagctg agacgcagca tggcacagtg ctggtgcagg ttaagtatga aggaactgat     180
gctccgtgta agatcccgtt cagtactcag gatgagaagg gtgtgaccca gaatggccgc     240
ttaattacag ccaaccctat cgtaactgac aaggagaagc ctgtgaacat cgagactgaa     300
ccacccttcg gtgagagtta tataatagtt ggcgccggag agaaggccct caagcttagc     360
tggtttcggc gcgacaagcg agataagctc caacttaagg gaatgtcata ctcaatgtgc     420
acaggtaagt tcaagatagt gaaggagata gccgagaccc agcatggcac catcgtgatc     480
agagtccaat atgaaggaga cgggtctcct tgtaagatcc cattcgagat aacagacttg     540
gagaagaggc acgtgctggg acgtctgata acagttaatc ccatagttac cgagaaggat     600
agccctgtta acattgaggc tgaacctccc ttcggagatt cctacattat tgtcggcgtg     660
gagccaggtc agctgaagct taactggttc agacgggaca agcgcgacaa gctgaagttg     720
aagggcatgt cctatgcaat gtgtctcaat actttcgttc tcaagaagga agtgagcgag     780
acacagcatg gcaccatatt aattaaggtt gagtacaagg gtgaggatgc tccttgcaag     840
attcctttca gcaccgagga tggacagggc aaggcccaca atggtcggct gatcaccgcc     900
aaccctgtgg taaccaagaa ggaagagccc gtcaacatag aagccgagcc gccgtttggc     960
gagtccaata tagtaatcgg catcggagat aaggccttga agattaattg gtacaggcgg    1020
gataagcgcg agaagttacg gattaagggt atgtcttaca ctatgtgtag cggtaagttt    1080
agcatcgaca aggagatggc agagacccag catggcacta ccgtggtcaa ggtgaagtac    1140
gaaggagctg gagcaccatg taaggtccct atcgagatcc gcgacgtgaa caaggagaag    1200
gtggtgggaa gaatcatctc ttccacacct ctggcagaga acacgaatag cgtgactaat    1260
atcgaacttg agcctccttt cggcgattcc tacatcgtta ttggcgtggg caactccgcc    1320
ctgacactgc attggttag acgtgacaag cgtagcgtgg cccttgcacc acacgtgggc    1380
ctaggcctgg agacgcgtac agagacatgg atgagcagtg aaggagcctg gaagcagatt    1440
cagaaggtcg agacctgggc tctcagacat ccttgagcgc gc                       1482
```

FIGURE 24 (SEQ ID NO : 29)

```
cgtacgatgc tcctaagcgt tccactgctt ctgggactgc tgggtttggc cgttgccgac     60
aagctcacgc tcaaggggat gagctacgtc atgtgcacag gctcattcaa gttggagaag    120
gaagtcgccg agacgcagca cggaacagta ctcgtgcagg tcaagtatga gggcaccgac    180
gctccatgca agatccgtt ctccacacag gacgagaagg gcgttactca gaacggaaga     240
ttaattactg ccaatcctat agtaacagac aaggagaagc ctgtgaatat tgagactgag    300
cctcccttcg gtgaatccta catcattgta ggggctggcg agaaggcttt gaagctctcc    360
tggtttgata agctgcagct caagggaatg tcgtattcaa tgtgcactgg gaagttcaag    420
attgtgaagg agattgcaga gactcaacac ggcaccattg tgataagggt ccagtacgag    480
ggtgatgggt caccctgcaa gattcccttt gagatcacag accttgagaa gaggcacgta    540
cttgggcgat taattaccgt gaatcctatt gtgactgaga aggatagtcc cgtgaacatt    600
gaagctgagc ctcctttcgg agatagctac attatcgtgg gagtcgagcc tggccagttg    660
aagctcaact ggtttgataa gctgaagctc aagggcatgt cctacgctat gtgcttgaat    720
acatttgtgc tgaagaagga ggtgagtgag acccaacacg gaaccatcct gatcaaggtg    780
gagtacaagg gtgaagatgc accttgcaag atcccttct ccactgaaga cgggcagggc     840
aaggcccata atgggagact cataacagct aatccagtgg tcaccaagaa ggaagaacca    900
gtcaacatcg aggcggagcc accatttggg gagagtaaca tcgtgatcgg tattggcgat    960
aaggccctga agattaactg gtatgagaag ttgagaatta aggggatgag ctataccatg   1020
tgctcaggta agttcagcat cgataaggag atggccgaga cacagcacgg gaccacagtt   1080
gtgaaggtga agtacgaggg cgctggggcc ccatgcaagg tgcctatcga gattcgcgac   1140
gtgaacaagg agaaggtcgt ggggcgaatc atctcatcca ccctctcgc agagaacacg    1200
aactctgtga ccaatattga gctggaacca ccttcggag actcatatat cgtcataggc    1260
gtcggcaatt cagctttgac attgcactgg ttcagacggg acaagcggtc cgttgccctg   1320
gctccacacg tcggcctggg ccttgagact aggacggaga cctggatgtc ctccgagggc   1380
gcctggaagc agatccagaa ggtggagacc tgggccctgc gccacccctg ataggcgcgc   1440
```

TetraDV-C

CRT signal sequence + DV-1 EDIII + ectoM DV-1 + DV-2 EDIII + ectoM DV-2 + DV-3 EDIII + ectoM DV-3 + DV-4 EDIII + ectoM DV-4 (624aa, rule of 6 ok, furin sites underlined)

DEN-1 ectoM-D1  DEN-2 ectoM-D2  DEN-3 ectoM-D3  DEN-4 ectoM-D4
EDIII          EDIII           EDIII           EDIII

*FIG. 27*

TetraDV-D

CRT signal sequence + DV-1 EDIII + DV-2 EDIII + DV-3 EDIII + DV-4 EDIII + ectoM DV-1
(489aa add 3 nucleotides for rule of 6)

DEN-1 EDIII, DEN-2 EDIII, DEN-3 EDIII, DEN-4 EDIII, ectoM-D1

FIG. 28

TetraDV-E

CRT signal sequence + DV-1 EDIII - DV-2 EDIII - DV-3 EDIII - DV-4 EDIII + ectoM DV-1
(474aa, rule of 6 ok, furin site underlined)

ectoM-D1

DEN-1  DEN-2  DEN-3  DEN-4
EDIII  EDIII  EDIII  EDIII

DV-1 (FGA89)    (SEQ ID NO : 30)
SVALAPHVGLGLETRTETWMSSEGAWKQIQKVETWALRHP

DV-3 (PAH881)    (SEQ ID NO : 31)
SVALAPHVGMGLDTRTQTWMSAEGAWRQVEKVETWALRHP

DV-4 (63632)    (SEQ ID NO : 32)
SVALTPHSGMGLETRAETWMSSEGAWKHAQRVESWILRNP

DV-2 (Jam/Camb)  (SEQ ID NO : 33)
SVALVPHVGMGLETRTETWMSSEGAWKHAQRIETWILRHP

SEQUENCE LISTING

<160> NUMBER OF SEQ ID NOS: 35

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 1

Met Leu Leu Ser Val Pro Leu Leu Gly Leu Leu Gly Leu Ala Val
1               5                   10                  15

Ala Arg Ser Lys Gly Met Ser Tyr Val Met Cys Thr Gly Ser Phe Lys
            20                  25                  30

Leu Glu Lys Glu Val Ala Glu Thr Gln His Gly Thr Val Leu Val Gln
        35                  40                  45

Val Lys Tyr Glu Gly Thr Asp Ala Pro Cys Lys Ile Pro Phe Ser Thr
    50                  55                  60

Gln Asp Glu Lys Gly Val Thr Gln Asn Gly Arg Leu Ile Thr Ala Asn
 65                 70                  75                  80

Pro Ile Val Thr Asp Lys Glu Lys Pro Val Asn Ile Glu Thr Glu Pro
                85                  90                  95

Pro Phe Gly Glu Ser Tyr Ile Val Gly Ala Gly Lys Ala Leu
            100                 105                 110

Lys Leu Ser Trp Phe Lys Arg
        115

<210> SEQ ID NO 2
<211> LENGTH: 384
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains
<220> FEATURE:
<221> NAME/KEY: CDS
<222> LOCATION: (7)..(363)

<400> SEQUENCE: 2 cgtacg atg ctg cta tcc gtg ccg ttg ctg ctc ggc ctc ctc ggc ctg       48
       Met Leu Leu Ser Val Pro Leu Leu Leu Gly Leu Leu Gly Leu
       1               5                   10 gcc gtc gcc aga tct aaa ggg atg tca tat gtg atg tgc aca ggc tca      96
Ala Val Ala Arg Ser Lys Gly Met Ser Tyr Val Met Cys Thr Gly Ser
15                  20                  25                  30 ttt aag cta gag aag gaa gtg gct gag acc cag cat ggg act gtc cta    144
Phe Lys Leu Glu Lys Glu Val Ala Glu Thr Gln His Gly Thr Val Leu
                35                  40                  45 gtg cag gtt aaa tac gaa gga aca gat gcg cca tgc aag atc ccc ttt    192
Val Gln Val Lys Tyr Glu Gly Thr Asp Ala Pro Cys Lys Ile Pro Phe
            50                  55                  60 tcg acc caa gat gag aaa gga gtg acc cag aat ggg aga ttg ata aca    240
Ser Thr Gln Asp Glu Lys Gly Val Thr Gln Asn Gly Arg Leu Ile Thr
65                  70                  75 gcc aat ccc ata gtt act gac aaa gaa aaa cca gtc aac att gag aca    288
Ala Asn Pro Ile Val Thr Asp Lys Glu Lys Pro Val Asn Ile Glu Thr
80                  85                  90 gaa cca cct ttt ggt gag agc tac atc ata gta ggg gca ggt gaa aaa    336
Glu Pro Pro Phe Gly Glu Ser Tyr Ile Ile Val Gly Ala Gly Glu Lys
95                 100                 105                 110 gct ttg aaa cta agc tgg ttc aag cga tagcggccgc tataagcgcg c        384
Ala Leu Lys Leu Ser Trp Phe Lys Arg
                115

<210> SEQ ID NO 3
<211> LENGTH: 162
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 3

Met Leu Leu Ser Val Pro Leu Leu Leu Gly Leu Leu Gly Leu Ala Val
1               5                   10                  15

Ala Arg Ser Lys Gly Met Ser Tyr Val Met Cys Thr Gly Ser Phe Lys
            20                  25                  30

Leu Glu Lys Glu Val Ala Glu Thr Gln His Gly Thr Val Leu Val Gln
        35                  40                  45

```
Val Lys Tyr Glu Gly Thr Asp Ala Pro Cys Lys Ile Pro Phe Ser Thr
 50                  55                  60

Gln Asp Glu Lys Gly Val Thr Gln Asn Gly Arg Leu Ile Thr Ala Asn
 65                  70                  75                  80

Pro Ile Val Thr Asp Lys Glu Lys Pro Val Asn Ile Glu Thr Glu Pro
                 85                  90                  95

Pro Phe Gly Glu Ser Tyr Ile Ile Val Gly Ala Gly Glu Lys Ala Leu
            100                 105                 110

Lys Leu Ser Trp Phe Arg Arg Asp Lys Arg Ser Val Ala Leu Ala Pro
                115                 120                 125

His Val Gly Leu Gly Leu Glu Thr Arg Thr Glu Thr Trp Met Ser Ser
130                 135                 140

Glu Gly Ala Trp Lys Gln Ile Gln Lys Val Glu Thr Trp Ala Leu Arg
145                 150                 155                 160

His Pro
```

<210> SEQ ID NO 4
<211> LENGTH: 516
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains
<220> FEATURE:
<221> NAME/KEY: CDS
<222> LOCATION: (7)..(492)

<400> SEQUENCE: 4

```
cgtacg atg ctg cta tcc gtg ccg ttg ctg ctc ggc ctc ctc ggc ctg        48
       Met Leu Leu Ser Val Pro Leu Leu Leu Gly Leu Leu Gly Leu
         1               5                  10 gcc gtc gcc aga tct aaa ggg atg tca tat gtg atg tgc aca ggc tca        96
Ala Val Ala Arg Ser Lys Gly Met Ser Tyr Val Met Cys Thr Gly Ser
 15              20                  25                  30 ttt aag cta gag aag gaa gtg gct gag acc cag cat ggg act gtc cta       144
Phe Lys Leu Glu Lys Glu Val Ala Glu Thr Gln His Gly Thr Val Leu
             35                  40                  45 gtg cag gtt aaa tac gaa gga aca gat gcg cca tgc aag atc ccc ttt       192
Val Gln Val Lys Tyr Glu Gly Thr Asp Ala Pro Cys Lys Ile Pro Phe
         50                  55                  60 tcg acc caa gat gag aaa gga gtg acc cag aat ggg aga ttg ata aca       240
Ser Thr Gln Asp Glu Lys Gly Val Thr Gln Asn Gly Arg Leu Ile Thr
     65                  70                  75 gcc aat ccc ata gtt act gac aaa gaa aaa cca gtc aac att gag aca       288
Ala Asn Pro Ile Val Thr Asp Lys Glu Lys Pro Val Asn Ile Glu Thr
 80                  85                  90 gaa cca cct ttt ggt gag agc tac atc ata gta ggg gca ggt gaa aaa       336
Glu Pro Pro Phe Gly Glu Ser Tyr Ile Ile Val Gly Ala Gly Glu Lys
 95                 100                 105                 110 gct ttg aaa cta agc tgg ttc cga cga gac aaa cgt tcc gtg gca ctg       384
Ala Leu Lys Leu Ser Trp Phe Arg Arg Asp Lys Arg Ser Val Ala Leu
                115                 120                 125 gcc cca cac gtg gga ctt ggt cta gaa aca aga acc gaa aca tgg atg       432
Ala Pro His Val Gly Leu Gly Leu Glu Thr Arg Thr Glu Thr Trp Met
            130                 135                 140 tcc tct gaa ggc gcc tgg aaa caa ata caa aaa gtg gag act tgg gct       480
Ser Ser Glu Gly Ala Trp Lys Gln Ile Gln Lys Val Glu Thr Trp Ala
145                 150                 155 ttg aga cac cca tgatagcggc cgctataagc gcgc                            516
Leu Arg His Pro
```

<210> SEQ ID NO 5
<211> LENGTH: 516
<212> TYPE: DNA
<213> ORGANISM: Artificial Sequence
<220> FEATURE:
<223> OTHER INFORMATION: Description of Artificial Sequence: Synthetic fusion sequence comprising domain(s) of Flaviviridae strains

<400> SEQUENCE: 5

```
cgtacgatgc tgctatccgt gccgttgctg ctcggcctcc tcggcctggc cgtcgccaga      60
tctaaaggga tgtcatatgt gatgtgcaca ggctcattta agctagagaa ggaagtggct     120
gagacccagc atgggactgt cctagtgcag gttaaatacg aaggaacaga tgcgccatgc     180
aagatcccct tttcgaccca agatgagaaa ggagtgaccc agaatgggag attgataaca     240
gccaatccca tagttactga caaagaaaaa ccagtcaaca ttgagacaga accaccttt      300
ggtgagagct acatcatagt aggggcaggt gaaaaagctt tgaaactaag ctggttccga     360
cgagacaaac gttccgtggc actggcccca cacgtgggac ttggtctaga aacaagaacc     420
gaaacatgga tgtcctctga aggcgcctgg aaacaaatac aaaaagtgga gacttgggct     480
ttgagacacc catgatagcg gccgctataa gcgcgc                               516
```

<210> SEQ ID NO 6
<211> LENGTH: 168
<212> TYPE: PRT
<213> ORGANISM: Artificial Sequence
<220> FEATURE:
<223> OTHER INFORMATION: Description of Artificial Sequence: Synthetic fusion sequence comprising domain(s) of Flaviviridae strains

<400> SEQUENCE: 6

Arg Thr Met Leu Leu Ser Val Pro Leu Leu Gly Leu Leu Gly Leu
1               5                   10                  15

Ala Val Ala Arg Ser Lys Gly Thr Thr Tyr Gly Met Cys Thr Glu Lys
            20                  25                  30

Phe Ser Phe Ala Lys Asn Pro Ala Asp Thr Gly His Gly Thr Val Val
        35                  40                  45

Ile Glu Leu Ser Tyr Ser Gly Ser Asp Gly Pro Cys Lys Ile Pro Ile
    50                  55                  60

Val Ser Val Ala Ser Leu Asn Asp Met Thr Pro Val Gly Arg Leu Val
65                  70                  75                  80

Thr Val Asn Pro Phe Val Ala Thr Ser Ser Ala Asn Ser Lys Val Leu
                85                  90                  95

Val Glu Met Glu Pro Pro Phe Gly Asp Ser Tyr Ile Val Val Gly Arg
            100                 105                 110

Gly Asp Lys Gln Ile Asn His His Trp His Lys Lys Arg Ser Arg Arg
        115                 120                 125

Ser Val Ser Val Gln Thr His Gly Glu Ser Ser Leu Val Asn Lys Lys
    130                 135                 140

Glu Ala Trp Leu Asp Ser Thr Lys Ala Thr Arg Tyr Leu Met Lys Thr
145                 150                 155                 160

Glu Asn Trp Ile Val Arg Asn Pro
                165

<210> SEQ ID NO 7
<211> LENGTH: 528
<212> TYPE: DNA

<213> ORGANISM: Artificial Sequence
<220> FEATURE:
<223> OTHER INFORMATION: Description of Artificial Sequence: Synthetic
      fusion sequence comprising domain(s) of Flaviviridae strains
<220> FEATURE:
<221> NAME/KEY: CDS
<222> LOCATION: (1)..(504)

<400> SEQUENCE: 7

```
cgt acg atg ctg cta tcc gtg ccg ttg ctg ctc ggc ctc ctc ggc ctg        48
Arg Thr Met Leu Leu Ser Val Pro Leu Leu Leu Gly Leu Leu Gly Leu
1               5                   10                  15 gcc gtc gcc aga tct aaa ggc aca acc tat ggc atg tgc aca gaa aaa        96
Ala Val Ala Arg Ser Lys Gly Thr Thr Tyr Gly Met Cys Thr Glu Lys
            20                  25                  30 ttc tcg ttc gcg aaa aat ccg gcg gac act ggt cac gga aca gtt gtc       144
Phe Ser Phe Ala Lys Asn Pro Ala Asp Thr Gly His Gly Thr Val Val
        35                  40                  45 att gaa ctt tcc tac tct ggg agt gat ggc cct tgc aaa att ccg att       192
Ile Glu Leu Ser Tyr Ser Gly Ser Asp Gly Pro Cys Lys Ile Pro Ile
    50                  55                  60 gtc tcc gtt gcg agc ctc aat gac atg acc ccc gtc ggg cgg ctg gtg       240
Val Ser Val Ala Ser Leu Asn Asp Met Thr Pro Val Gly Arg Leu Val
65                  70                  75                  80 aca gtg aac ccc ttc gtc gcg act tcc agc gcc aac tca aag gtg cta       288
Thr Val Asn Pro Phe Val Ala Thr Ser Ser Ala Asn Ser Lys Val Leu
                85                  90                  95 gtc gag atg gaa ccc ccc ttc gga gac tcc tac atc gta gtt gga agg       336
Val Glu Met Glu Pro Pro Phe Gly Asp Ser Tyr Ile Val Val Gly Arg
            100                 105                 110 gga gac aag cag atc aac cac cat tgg cac aaa aag cga agc agg aga       384
Gly Asp Lys Gln Ile Asn His His Trp His Lys Lys Arg Ser Arg Arg
        115                 120                 125 tcc gtg tcg gtc caa aca cat ggg gag agt tca cta gtg aat aaa aaa       432
Ser Val Ser Val Gln Thr His Gly Glu Ser Ser Leu Val Asn Lys Lys
    130                 135                 140 gag gct tgg ctg gat tca acg aaa gcc aca cga tac ctc atg aaa act       480
Glu Ala Trp Leu Asp Ser Thr Lys Ala Thr Arg Tyr Leu Met Lys Thr
145                 150                 155                 160 gag aac tgg atc gta agg aat cct tgatagcggc cgctataagc gcgc            528
Glu Asn Trp Ile Val Arg Asn Pro
                165
```

<210> SEQ ID NO 8
<211> LENGTH: 262
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 8

```
Arg Thr Met Leu Leu Ser Val Pro Leu Leu Leu Gly Leu Leu Gly Leu
1               5                   10                  15

Ala Val Ala Arg Ser Lys Gly Met Ser Tyr Val Met Cys Thr Gly Ser
            20                  25                  30

Phe Lys Leu Glu Lys Glu Val Ala Glu Thr Gln His Gly Thr Val Leu
        35                  40                  45

Val Gln Val Lys Tyr Glu Gly Thr Asp Ala Pro Cys Lys Ile Pro Phe
    50                  55                  60

Ser Thr Gln Asp Glu Lys Gly Val Thr Gln Asn Gly Arg Leu Ile Thr
65                  70                  75                  80
```

```
Ala Asn Pro Ile Val Thr Asp Lys Glu Lys Pro Val Asn Ile Glu Thr
             85                  90                  95

Glu Pro Pro Phe Gly Glu Ser Tyr Ile Ile Val Gly Ala Gly Glu Lys
            100                 105                 110

Ala Leu Lys Leu Ser Trp Phe Lys Gly Ser Ser Ile Gly Lys Met
        115                 120                 125

Phe Glu Ala Thr Ala Gly Gly Ser Gly Gly Lys Gly Met Ser Tyr Ser
130                 135                 140

Met Cys Thr Gly Lys Phe Lys Ile Val Lys Glu Ile Ala Glu Thr Gln
145                 150                 155                 160

His Gly Thr Ile Val Ile Arg Val Gln Tyr Glu Gly Asp Gly Ser Pro
                165                 170                 175

Cys Lys Ile Pro Phe Glu Ile Met Asp Leu Glu Lys Arg His Val Leu
                180                 185                 190

Gly Arg Leu Ile Thr Val Asn Pro Ile Val Thr Glu Lys Asp Ser Pro
                195                 200                 205

Val Asn Ile Glu Ala Glu Pro Pro Phe Gly Asp Ser Tyr Ile Ile Ile
        210                 215                 220

Gly Val Glu Pro Gly Gln Leu Lys Leu Asn Trp Phe Lys Lys Gly Ser
225                 230                 235                 240

Ser Ile Gly Gln Met Phe Glu Thr Thr Met Ser Gly Arg Val Glu Thr
                245                 250                 255

Trp Ala Leu Arg His Pro
                260

<210> SEQ ID NO 9
<211> LENGTH: 798
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains
<220> FEATURE:
<221> NAME/KEY: CDS
<222> LOCATION: (1)..(786)

<400> SEQUENCE: 9 cgt acg atg ctg cta tcc gtg ccg ttg ctg ctc ggc ctc ctc ggc ctg      48
Arg Thr Met Leu Leu Ser Val Pro Leu Leu Leu Gly Leu Leu Gly Leu
1               5                   10                  15 gcc gtc gcc aga tct aaa ggg atg tca tat gtg atg tgc aca ggc tca      96
Ala Val Ala Arg Ser Lys Gly Met Ser Tyr Val Met Cys Thr Gly Ser
            20                  25                  30 ttt aag cta gag aag gaa gtg gct gag acc cag cat ggg act gtc cta     144
Phe Lys Leu Glu Lys Glu Val Ala Glu Thr Gln His Gly Thr Val Leu
        35                  40                  45 gtg cag gtt aaa tac gaa gga aca gat gcg cca tgc aag atc ccc ttt     192
Val Gln Val Lys Tyr Glu Gly Thr Asp Ala Pro Cys Lys Ile Pro Phe
    50                  55                  60 tcg acc caa gat gag aaa gga gtg acc cag aat ggg aga ttg ata aca     240
Ser Thr Gln Asp Glu Lys Gly Val Thr Gln Asn Gly Arg Leu Ile Thr
65                  70                  75                  80 gcc aat ccc ata gtt act gac aaa gaa aaa cca gtc aac att gag aca     288
Ala Asn Pro Ile Val Thr Asp Lys Glu Lys Pro Val Asn Ile Glu Thr
                85                  90                  95 gaa cca cct ttt ggt gag agc tac atc ata gta ggg gca ggt gaa aaa     336
Glu Pro Pro Phe Gly Glu Ser Tyr Ile Ile Val Gly Ala Gly Glu Lys
            100                 105                 110
```

```
gct ttg aaa cta agc tgg ttc aag aaa gga agc agc ata ggg aaa atg      384
Ala Leu Lys Leu Ser Trp Phe Lys Lys Gly Ser Ser Ile Gly Lys Met
            115                 120                 125 ttc gaa gca acc gcc gga gga tca gga ggg aaa gga atg tca tac tct      432
Phe Glu Ala Thr Ala Gly Gly Ser Gly Gly Lys Gly Met Ser Tyr Ser
        130                 135                 140 atg tgt aca gga aag ttt aaa att gtg aag gaa ata gca gaa aca caa      480
Met Cys Thr Gly Lys Phe Lys Ile Val Lys Glu Ile Ala Glu Thr Gln
145                 150                 155                 160 cat gga aca ata gtt atc aga gta caa tat gaa ggg gac ggc tct cca      528
His Gly Thr Ile Val Ile Arg Val Gln Tyr Glu Gly Asp Gly Ser Pro
                165                 170                 175 tgt aag atc cct ttt gag ata atg gat ttg gaa aaa aga cac gtc tta      576
Cys Lys Ile Pro Phe Glu Ile Met Asp Leu Glu Lys Arg His Val Leu
            180                 185                 190 ggt cgc ctg att aca gtt aac ccg atc gta aca gaa aaa gat agc cca      624
Gly Arg Leu Ile Thr Val Asn Pro Ile Val Thr Glu Lys Asp Ser Pro
        195                 200                 205 gtc aac ata gaa gca gaa cct cca ttc gga gac agc tac atc atc ata      672
Val Asn Ile Glu Ala Glu Pro Pro Phe Gly Asp Ser Tyr Ile Ile Ile
210                 215                 220 gga gta gag ccg gga caa ttg aaa ctc aac tgg ttt aag aaa gga agt      720
Gly Val Glu Pro Gly Gln Leu Lys Leu Asn Trp Phe Lys Lys Gly Ser
225                 230                 235                 240 tcc atc ggc caa atg ttt gag aca aca atg agc ggc cgc gtg gag act      768
Ser Ile Gly Gln Met Phe Glu Thr Thr Met Ser Gly Arg Val Glu Thr
                245                 250                 255 tgg gct ttg aga cac cca tagtaagcgc gc                                798
Trp Ala Leu Arg His Pro
            260
```

```
<210> SEQ ID NO 10
<211> LENGTH: 262
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 10

Arg Thr Met Leu Leu Ser Val Pro Leu Leu Leu Gly Leu Leu Gly Leu
1               5                   10                  15

Ala Val Ala Arg Ser Lys Gly Met Ser Tyr Ala Met Cys Leu Asn Thr
            20                  25                  30

Phe Val Leu Lys Lys Glu Val Ser Glu Thr Gln His Gly Thr Ile Leu
        35                  40                  45

Ile Lys Val Glu Tyr Lys Gly Glu Asp Ala Pro Cys Lys Ile Pro Phe
    50                  55                  60

Ser Thr Glu Asp Gly Gln Gly Lys Ala His Asn Gly Arg Leu Ile Thr
65                  70                  75                  80

Ala Asn Pro Val Val Thr Lys Lys Glu Glu Pro Val Asn Ile Glu Ala
                85                  90                  95

Glu Pro Pro Phe Gly Glu Ser Asn Ile Val Ile Gly Ile Gly Asp Lys
            100                 105                 110

Ala Leu Lys Ile Asn Trp Tyr Lys Lys Gly Ser Ser Ile Gly Lys Met
        115                 120                 125

Phe Glu Ala Thr Ala Gly Gly Ser Gly Gly Lys Gly Met Ser Tyr Thr
    130                 135                 140

Met Cys Ser Gly Lys Phe Ser Ile Asp Lys Glu Met Ala Glu Thr Gln
```

-continued

```
            145                 150                 155                 160
His Gly Thr Thr Val Val Lys Val Lys Tyr Glu Gly Ala Gly Ala Pro
                        165                 170                 175

Cys Lys Val Pro Ile Glu Ile Arg Asp Val Asn Lys Glu Lys Val Val
            180                 185                 190

Gly Arg Ile Ile Ser Ser Thr Pro Phe Ala Glu Asn Thr Asn Ser Val
                195                 200                 205

Thr Asn Ile Glu Leu Gly Pro Pro Phe Gly Asp Ser Tyr Ile Val Ile
        210                 215                 220

Gly Val Gly Asp Ser Ala Leu Thr Leu His Trp Phe Arg Lys Gly Ser
225                 230                 235                 240

Ser Ile Gly Lys Met Phe Glu Ser Thr Tyr Ser Gly Arg Val Glu Thr
                    245                 250                 255

Trp Ala Leu Arg His Pro
                260
```

<210> SEQ ID NO 11
<211> LENGTH: 798
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains
<220> FEATURE:
<221> NAME/KEY: CDS
<222> LOCATION: (1)..(786)

<400> SEQUENCE: 11

```
cgt acg atg ctg cta tcc gtg ccg ttg ctg ctc ggc ctc ctc ggc ctg      48
Arg Thr Met Leu Leu Ser Val Pro Leu Leu Leu Gly Leu Leu Gly Leu
1               5                   10                  15 gcc gtc gcc aga tct aag ggg atg agc tat gca atg tgc ttg aat acc      96
Ala Val Ala Arg Ser Lys Gly Met Ser Tyr Ala Met Cys Leu Asn Thr
            20                  25                  30 ttt gtg ttg aag aaa gaa gtc tcc gaa acg cag cat ggg aca ata ctc     144
Phe Val Leu Lys Lys Glu Val Ser Glu Thr Gln His Gly Thr Ile Leu
        35                  40                  45 att aag gtt gag tac aaa ggg gaa gat gca cct tgc aag att cct ttc     192
Ile Lys Val Glu Tyr Lys Gly Glu Asp Ala Pro Cys Lys Ile Pro Phe
    50                  55                  60 tcc aca gag gat gga caa ggg aaa gct cac aat ggt aga ctg atc aca     240
Ser Thr Glu Asp Gly Gln Gly Lys Ala His Asn Gly Arg Leu Ile Thr
65                  70                  75                  80 gcc aac cca gtg gtg acc aag aag gag gag cct gtc aac att gag gct     288
Ala Asn Pro Val Val Thr Lys Lys Glu Glu Pro Val Asn Ile Glu Ala
                85                  90                  95 gaa cct cct ttt ggg gaa agt aac ata gtg att gga att gga gac aaa     336
Glu Pro Pro Phe Gly Glu Ser Asn Ile Val Ile Gly Ile Gly Asp Lys
            100                 105                 110 gcc ttg aaa att aac tgg tac aag aag gga agc tcg att ggg aag atg     384
Ala Leu Lys Ile Asn Trp Tyr Lys Lys Gly Ser Ser Ile Gly Lys Met
        115                 120                 125 ttc gag gcc act gcc ggt ggt tct ggt ggt aag gga atg tca tac acg     432
Phe Glu Ala Thr Ala Gly Gly Ser Gly Gly Lys Gly Met Ser Tyr Thr
    130                 135                 140 atg tgc tca gga aag ttc tca att gat aaa gag atg gca gaa aca cag     480
Met Cys Ser Gly Lys Phe Ser Ile Asp Lys Glu Met Ala Glu Thr Gln
145                 150                 155                 160 cat ggg aca aca gtg gtg aaa gtc aag tat gag ggt gct gga gct cca     528
His Gly Thr Thr Val Val Lys Val Lys Tyr Glu Gly Ala Gly Ala Pro
```

```
                         165                 170                 175
tgt aaa gtt ccc ata gag ata aga gat gtg aac aag gaa aaa gtg gtt       576
Cys Lys Val Pro Ile Glu Ile Arg Asp Val Asn Lys Glu Lys Val Val
            180                 185                 190 ggg cgt atc atc tca tct acc cct ttt gct gag aat acc aac agt gtg       624
Gly Arg Ile Ile Ser Ser Thr Pro Phe Ala Glu Asn Thr Asn Ser Val
        195                 200                 205 acc aat ata gaa ttg gaa ccc cct ttt ggg gat agc tac ata gta ata       672
Thr Asn Ile Glu Leu Glu Pro Pro Phe Gly Asp Ser Tyr Ile Val Ile
    210                 215                 220 ggt gta gga gac agt gca tta aca ctc cat tgg ttc agg aaa ggg agc       720
Gly Val Gly Asp Ser Ala Leu Thr Leu His Trp Phe Arg Lys Gly Ser
225                 230                 235                 240 tcc att ggc aag atg ttt gag tcc aca tac agc ggc cgc gtg gag act       768
Ser Ile Gly Lys Met Phe Glu Ser Thr Tyr Ser Gly Arg Val Glu Thr
                245                 250                 255 tgg gct ttg aga cac cca tagtaagcgc gc                                 798
Trp Ala Leu Arg His Pro
            260
```

<210> SEQ ID NO 12
<211> LENGTH: 132
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 12

```
Arg Thr Met Leu Leu Ser Val Pro Leu Leu Leu Gly Leu Leu Gly Leu
1               5                   10                  15

Ala Val Ala Arg Ser Lys Gly Met Ser Tyr Val Met Cys Thr Gly Ser
            20                  25                  30

Phe Lys Leu Glu Lys Glu Val Ala Glu Thr Gln His Gly Thr Val Leu
        35                  40                  45

Val Gln Val Lys Tyr Glu Gly Thr Asp Ala Pro Cys Lys Ile Pro Phe
    50                  55                  60

Ser Thr Gln Asp Glu Lys Gly Val Thr Gln Asn Gly Arg Leu Ile Thr
65                  70                  75                  80

Ala Asn Pro Ile Val Thr Asp Lys Glu Lys Pro Val Asn Ile Glu Thr
                85                  90                  95

Glu Pro Pro Phe Gly Glu Ser Tyr Ile Ile Val Gly Ala Gly Glu Lys
            100                 105                 110

Ala Leu Lys Leu Ser Trp Phe Lys Arg Gly Arg Ile Glu Thr Trp Ile
        115                 120                 125

Leu Arg His Pro
    130
```

<210> SEQ ID NO 13
<211> LENGTH: 408
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains
<220> FEATURE:
<221> NAME/KEY: CDS
<222> LOCATION: (1)..(396)

<400> SEQUENCE: 13

```
cgt acg atg ctg cta tcc gtg ccg ttg ctg ctc ggc ctc ctc ggc ctg       48
```

```
Arg Thr Met Leu Leu Ser Val Pro Leu Leu Leu Gly Leu Leu Gly Leu
1               5                   10                  15 gcc gtc gcc aga tct aaa ggg atg tca tat gtg atg tgc aca ggc tca         96
Ala Val Ala Arg Ser Lys Gly Met Ser Tyr Val Met Cys Thr Gly Ser
            20                  25                  30 ttt aag cta gag aag gaa gtg gct gag acc cag cat ggg act gtc cta        144
Phe Lys Leu Glu Lys Glu Val Ala Glu Thr Gln His Gly Thr Val Leu
        35                  40                  45 gtg cag gtt aaa tac gaa gga aca gat gcg cca tgc aag atc ccc ttt        192
Val Gln Val Lys Tyr Glu Gly Thr Asp Ala Pro Cys Lys Ile Pro Phe
50                  55                  60 tcg acc caa gat gag aaa gga gtg acc cag aat ggg aga ttg ata aca        240
Ser Thr Gln Asp Glu Lys Gly Val Thr Gln Asn Gly Arg Leu Ile Thr
65                  70                  75                  80 gcc aat ccc ata gtt act gac aaa gaa aaa cca gtc aac att gag aca        288
Ala Asn Pro Ile Val Thr Asp Lys Glu Lys Pro Val Asn Ile Glu Thr
                85                  90                  95 gaa cca cct ttt ggt gag agc tac atc ata gta ggg gca ggt gaa aaa        336
Glu Pro Pro Phe Gly Glu Ser Tyr Ile Ile Val Gly Ala Gly Glu Lys
            100                 105                 110 gct ttg aaa cta agc tgg ttc aag cgc ggc cgc att gaa acc tgg atc        384
Ala Leu Lys Leu Ser Trp Phe Lys Arg Gly Arg Ile Glu Thr Trp Ile
        115                 120                 125 ttg aga cat cca tagtaagcgc gc                                          408
Leu Arg His Pro
        130

<210> SEQ ID NO 14
<211> LENGTH: 123
<212> TYPE: PRT
<213> ORGANISM: Flavivirus sp.

<400> SEQUENCE: 14

Arg Thr Met Leu Leu Ser Val Pro Leu Leu Leu Gly Leu Leu Gly Leu
1               5                   10                  15

Ala Val Ala Arg Ser Lys Gly Thr Thr Tyr Gly Met Cys Thr Glu Lys
            20                  25                  30

Phe Ser Phe Ala Lys As

```
Arg Thr Met Leu Leu Ser Val Pro Leu Leu Leu Gly Leu Leu Gly Leu
1               5                   10                  15 gcc gtc gcc aga tct aaa ggc aca acc tat ggc atg tgc aca gaa aaa        96
Ala Val Ala Arg Ser Lys Gly Thr Thr Tyr Gly Met Cys Thr Glu Lys
            20                  25                  30 ttc tcg ttc gcg aaa aat ccg gcg gac act ggt cac gga aca gtt gtc       144
Phe Ser Phe Ala Lys Asn Pro Ala Asp Thr Gly His Gly Thr Val Val
            35                  40                  45 att gaa ctt tcc tac tct ggg agt gat ggc cct tgc aaa att ccg att       192
Ile Glu Leu Ser Tyr Ser Gly Ser Asp Gly Pro Cys Lys Ile Pro Ile
50                      55                  60 gtc tcc gtt gcg agc ctc aat gac atg acc ccc gtc ggg cgg ctg gtg       240
Val Ser Val Ala Ser Leu Asn Asp Met Thr Pro Val Gly Arg Leu Val
65                  70                  75                  80 aca gtg aac ccc ttc gtc gcg act tcc agc gcc aac tca aag gtg cta       288
Thr Val Asn Pro Phe Val Ala Thr Ser Ser Ala Asn Ser Lys Val Leu
                85                  90                  95 gtc gag atg gaa ccc ccc ttc gga gac tcc tac atc gta gtt gga agg       336
Val Glu Met Glu Pro Pro Phe Gly Asp Ser Tyr Ile Val Val Gly Arg
                100                 105                 110 gga gac aag cag atc aac cac cat tgg cac aaa tagcggccgc tataagcgcg     389
Gly Asp Lys Gln Ile Asn His His Trp His Lys
                115                 120 c                                                                     390

<210> SEQ ID NO 16
<211> LENGTH: 494
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 16

Arg Thr Met Leu Leu Ser Val Pro Leu Leu Leu Gly Leu Leu Gly Leu
1               5                   10                  15

Ala Val Ala Arg Ser Lys Gly Met Ser Tyr Val Met Cys Thr Gly Ser
            20                  25                  30

Phe Lys Leu Glu Lys Glu Val Ala Glu Thr Gln His Gly Thr Val Leu
            35                  40                  45

Val Gln Val Lys Tyr Glu Gly Thr Asp Ala Pro Cys Lys Ile Pro Phe
        50                  55                  60

Ser Thr Gln Asp Glu Lys Gly Val Thr Gln Asn Gly Arg Leu Ile Thr
65                  70                  75                  80

Ala Asn Pro Ile Val Thr Asp Lys Glu Lys Pro Val Asn Ile Glu Thr
                85                  90                  95

Glu Pro Pro Phe Gly Glu Ser Tyr Ile Ile Val Gly Ala Gly Glu Lys
                100                 105                 110

Ala Leu Lys Leu Ser Trp Phe Lys Lys Gly Ser Ser Ile Gly Lys Met
            115                 120                 125

Phe Glu Ala Thr Ala Gly Gly Ser Gly Gly Lys Gly Met Ser Tyr Ser
        130                 135                 140

Met Cys Thr Gly Lys Phe Lys Ile Val Lys Glu Ile Ala Glu Thr Gln
145                 150                 155                 160

His Gly Thr Ile Val Ile Arg Val Gln Tyr Glu Gly Asp Gly Ser Pro
                165                 170                 175

Cys Lys Ile Pro Phe Glu Ile Met Asp Leu Glu Lys Arg His Val Leu
            180                 185                 190
```

```
Gly Arg Leu Ile Thr Val Asn Pro Ile Val Thr Glu Lys Asp Ser Pro
            195                 200                 205
Val Asn Ile Glu Ala Glu Pro Pro Phe Gly Asp Ser Tyr Ile Ile Ile
210                 215                 220
Gly Val Glu Pro Gly Gln Leu Lys Leu Asn Trp Phe Lys Lys Gly Ser
225                 230                 235                 240
Ser Ile Gly Gln Met Phe Glu Thr Thr Met Gly Gly Ser Lys Gly Met
            245                 250                 255
Ser Tyr Ala Met Cys Leu Asn Thr Phe Val Leu Lys Lys Glu Val Ser
                260                 265                 270
Glu Thr Gln His Gly Thr Ile Leu Ile Lys Val Glu Tyr Lys Gly Glu
            275                 280                 285
Asp Ala Pro Cys Lys Ile Pro Phe Ser Thr Glu Asp Gly Gln Gly Lys
        290                 295                 300
Ala His Asn Gly Arg Leu Ile Thr Ala Asn Pro Val Val Thr Lys Lys
305                 310                 315                 320
Glu Glu Pro Val Asn Ile Glu Ala Glu Pro Pro Phe Gly Glu Ser Asn
                325                 330                 335
Ile Val Ile Gly Ile Gly Asp Lys Ala Leu Lys Ile Asn Trp Tyr Lys
            340                 345                 350
Lys Gly Ser Ser Ile Gly Lys Met Phe Glu Ala Thr Ala Gly Gly Ser
        355                 360                 365
Gly Gly Lys Gly Met Ser Tyr Thr Met Cys Ser Gly Lys Phe Ser Ile
370                 375                 380
Asp Lys Glu Met Ala Glu Thr Gln His Gly Thr Thr Val Val Lys Val
385                 390                 395                 400
Lys Tyr Glu Gly Ala Gly Ala Pro Cys Lys Val Pro Ile Glu Ile Arg
                405                 410                 415
Asp Val Asn Lys Glu Lys Val Val Gly Arg Ile Ile Ser Ser Thr Pro
            420                 425                 430
Phe Ala Glu Asn Thr Asn Ser Val Thr Asn Ile Glu Leu Glu Pro Pro
        435                 440                 445
Phe Gly Asp Ser Tyr Ile Val Ile Gly Val Gly Asp Ser Ala Leu Thr
    450                 455                 460
Leu His Trp Phe Arg Lys Gly Ser Ser Ile Gly Lys Met Phe Glu Ser
465                 470                 475                 480
Thr Tyr Ser Gly Arg Val Glu Thr Trp Ala Leu Arg His Pro
                485                 490

<210> SEQ ID NO 17
<211> LENGTH: 1494
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains
<220> FEATURE:
<221> NAME/KEY: CDS
<222> LOCATION: (1)..(1482)

<400> SEQUENCE: 17 cgt acg atg ctg cta tcc gtg ccg ttg ctg ctc ggc ctc ctc ggc ctg       48
Arg Thr Met Leu Leu Ser Val Pro Leu Leu Leu Gly Leu Leu Gly Leu
1               5                   10                  15 gcc gtc gcc aga tct aaa ggg atg tca tat gtg atg tgc aca ggc tca       96
Ala Val Ala Arg Ser Lys Gly Met Ser Tyr Val Met Cys Thr Gly Ser
            20                  25                  30
```

-continued

| | | |
|---|---|---|
| ttt aag cta gag aag gaa gtg gct gag acc cag cat ggg act gtc cta<br>Phe Lys Leu Glu Lys Glu Val Ala Glu Thr Gln His Gly Thr Val Leu<br>35                   40                   45 | 144 |
| gtg cag gtt aaa tac gaa gga aca gat gcg cca tgc aag atc ccc ttt<br>Val Gln Val Lys Tyr Glu Gly Thr Asp Ala Pro Cys Lys Ile Pro Phe<br>50                   55                   60 | 192 |
| tcg acc caa gat gag aaa gga gtg acc cag aat ggg aga ttg ata aca<br>Ser Thr Gln Asp Glu Lys Gly Val Thr Gln Asn Gly Arg Leu Ile Thr<br>65                   70                   75                 80 | 240 |
| gcc aat ccc ata gtt act gac aaa gaa aaa cca gtc aac att gag aca<br>Ala Asn Pro Ile Val Thr Asp Lys Glu Lys Pro Val Asn Ile Glu Thr<br>                   85                   90                 95 | 288 |
| gaa cca cct ttt ggt gag agc tac atc ata gta ggg gca ggt gaa aaa<br>Glu Pro Pro Phe Gly Glu Ser Tyr Ile Ile Val Gly Ala Gly Glu Lys<br>                  100                105             110 | 336 |
| gct ttg aaa cta agc tgg ttc aag aaa gga agc agc ata ggg aaa atg<br>Ala Leu Lys Leu Ser Trp Phe Lys Lys Gly Ser Ser Ile Gly Lys Met<br>            115                120                125 | 384 |
| ttc gaa gca acc gcc gga gga tca gga ggg aaa gga atg tca tac tct<br>Phe Glu Ala Thr Ala Gly Gly Ser Gly Gly Lys Gly Met Ser Tyr Ser<br>130                  135                140 | 432 |
| atg tgt aca gga aag ttt aaa att gtg aag gaa ata gca gaa aca caa<br>Met Cys Thr Gly Lys Phe Lys Ile Val Lys Glu Ile Ala Glu Thr Gln<br>145                  150                155                160 | 480 |
| cat gga aca ata gtt atc aga gta caa tat gaa ggg gac ggc tct cca<br>His Gly Thr Ile Val Ile Arg Val Gln Tyr Glu Gly Asp Gly Ser Pro<br>                  165                170             175 | 528 |
| tgt aag atc cct ttt gag ata atg gat ttg gaa aaa aga cac gtc tta<br>Cys Lys Ile Pro Phe Glu Ile Met Asp Leu Glu Lys Arg His Val Leu<br>            180                185                190 | 576 |
| ggt cgc ctg att aca gtt aac ccg atc gta aca gaa aaa gat agc cca<br>Gly Arg Leu Ile Thr Val Asn Pro Ile Val Thr Glu Lys Asp Ser Pro<br>               195                200              205 | 624 |
| gtc aac ata gaa gca gaa cct cca ttc gga gac agc tac atc atc ata<br>Val Asn Ile Glu Ala Glu Pro Pro Phe Gly Asp Ser Tyr Ile Ile Ile<br>210                  215                220 | 672 |
| gga gta gag ccg gga caa ttg aaa ctc aac tgg ttt aag aaa gga agt<br>Gly Val Glu Pro Gly Gln Leu Lys Leu Asn Trp Phe Lys Lys Gly Ser<br>225                  230                235                240 | 720 |
| tcc atc ggc caa atg ttt gag aca aca atg gga gga tct aag ggg atg<br>Ser Ile Gly Gln Met Phe Glu Thr Thr Met Gly Gly Ser Lys Gly Met<br>                  245                250                255 | 768 |
| agc tat gca atg tgc ttg aat acc ttt gtg ttg aag aaa gaa gtc tcc<br>Ser Tyr Ala Met Cys Leu Asn Thr Phe Val Leu Lys Lys Glu Val Ser<br>            260                265                270 | 816 |
| gaa acg cag cat ggg aca ata ctc att aag gtt gag tac aaa ggg gaa<br>Glu Thr Gln His Gly Thr Ile Leu Ile Lys Val Glu Tyr Lys Gly Glu<br>               275                280              285 | 864 |
| gat gca cct tgc aag att cct ttc tcc aca gag gat gga caa ggg aaa<br>Asp Ala Pro Cys Lys Ile Pro Phe Ser Thr Glu Asp Gly Gln Gly Lys<br>290                  295                300 | 912 |
| gct cac aat ggt aga ctg atc aca gcc aac cca gtg gtg acc aag aag<br>Ala His Asn Gly Arg Leu Ile Thr Ala Asn Pro Val Val Thr Lys Lys<br>305                  310                315                320 | 960 |
| gag gag cct gtc aac att gag gct gaa cct cct ttt ggg gaa agt aac<br>Glu Glu Pro Val Asn Ile Glu Ala Glu Pro Pro Phe Gly Glu Ser Asn<br>                  325                330                335 | 1008 |
| ata gtg att gga att gga gac aaa gcc ttg aaa att aac tgg tac aag<br>Ile Val Ile Gly Ile Gly Asp Lys Ala Leu Lys Ile Asn Trp Tyr Lys | 1056 |

-continued

```
            340                 345                 350 aag gga agc tcg att ggg aag atg ttc gag gcc act gcc ggt ggt tct     1104
Lys Gly Ser Ser Ile Gly Lys Met Phe Glu Ala Thr Ala Gly Gly Ser
        355                 360                 365 ggt ggt aag gga atg tca tac acg atg tgc tca gga aag ttc tca att     1152
Gly Gly Lys Gly Met Ser Tyr Thr Met Cys Ser Gly Lys Phe Ser Ile
    370                 375                 380 gat aaa gag atg gca gaa aca cag cat ggg aca aca gtg gtg aaa gtc     1200
Asp Lys Glu Met Ala Glu Thr Gln His Gly Thr Thr Val Val Lys Val
385                 390                 395                 400 aag tat gag ggt gct gga gct cca tgt aaa gtt ccc ata gag ata aga     1248
Lys Tyr Glu Gly Ala Gly Ala Pro Cys Lys Val Pro Ile Glu Ile Arg
                405                 410                 415 gat gtg aac aag gaa aaa gtg gtt ggg cgt atc atc tca tct acc cct     1296
Asp Val Asn Lys Glu Lys Val Val Gly Arg Ile Ile Ser Ser Thr Pro
            420                 425                 430 ttt gct gag aat acc aac agt gtg acc aat ata gaa ttg gaa ccc cct     1344
Phe Ala Glu Asn Thr Asn Ser Val Thr Asn Ile Glu Leu Glu Pro Pro
        435                 440                 445 ttt ggg gat agc tac ata gta ata ggt gta gga gac agt gca tta aca     1392
Phe Gly Asp Ser Tyr Ile Val Ile Gly Val Gly Asp Ser Ala Leu Thr
    450                 455                 460 ctc cat tgg ttc agg aaa ggg agc tcc att ggc aag atg ttt gag tcc     1440
Leu His Trp Phe Arg Lys Gly Ser Ser Ile Gly Lys Met Phe Glu Ser
465                 470                 475                 480 aca tac agc ggc cgc gtg gag act tgg gct ttg aga cac cca             1482
Thr Tyr Ser Gly Arg Val Glu Thr Trp Ala Leu Arg His Pro
                485                 490 tagtaagcgc gc                                                       1494

<210> SEQ ID NO 18
<211> LENGTH: 390
<212> TYPE: DNA
<213> ORGANISM: Flavivirus sp.

<400> SEQUENCE: 18
cgtacgatgc tgctatccgt gccgttgctg ctcggcctcc tcggcctggc cgtcgccaga     60
tctaagggaa caacctatgg cgtctgttca aaggctttca agtttcttgg gactcccgca    120
gacacaggtc acggcactgt ggtgttggaa ttgcagtaca ctggcacgga tggaccttgc    180
aaagttccta tctcgtcagt ggcttcattg aacgacctaa cgccagtggg cagattggtc    240
actgtcaacc cttttgtttc agtggccacg gccaacgcta aggtcctgat tgaattggaa    300
ccaccctttg gagactcata catagtggtg ggcagaggag aacaacagat taatcaccat    360
tggcacaagt agcggccgct ataagcgcgc                                     390

<210> SEQ ID NO 19
<211> LENGTH: 528
<212> TYPE: DNA
<213> ORGANISM: Flavivirus sp.

<400> SEQUENCE: 19
cgtacgatgc tgctatccgt gccgttgctg ctcggcctcc tcggcctggc cgtcgccaga     60
tctaagggaa caacctatgg cgtctgttca aaggctttca agtttcttgg gactcccgca    120
gacacaggtc acggcactgt ggtgttggaa ttgcagtaca ctggcacgga tggaccttgc    180
aaagttccta tctcgtcagt ggcttcattg aacgacctaa cgccagtggg cagattggtc    240
actgtcaacc cttttgtttc agtggccacg gccaacgcta aggtcctgat tgaattggaa    300
```

```
ccacccttg gagactcata catagtggtg ggcagaggag aacaacagat taatcaccat    360
tggcacaaga gacgcagtcg gaggtcactg acagtgcaga cacacggaga aagcactcta    420
gcgaacaaga agggggcttg gatggacagc accaaggcca caaggtattt ggtaaaaaca    480
gaatcatgga tcttgaggaa cccttgatag cggccgctat aagcgcgc               528
```

<210> SEQ ID NO 20
<211> LENGTH: 624
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 20

Met Leu Leu Ser Val Pro Leu Leu Gly Leu Leu Gly Leu Ala Val
1               5                   10                  15

Ala Asp Lys Leu Thr Leu Lys Gly Met Ser Tyr Val Met Cys Thr Gly
            20                  25                  30

Ser Phe Lys Leu Glu Lys Glu Val Ala Glu Thr Gln His Gly Thr Val
        35                  40                  45

Leu Val Gln Val Lys Tyr Glu Gly Thr Asp Ala Pro Cys Lys Ile Pro
    50                  55                  60

Phe Ser Thr Gln Asp Glu Lys Gly Val Thr Gln Asn Gly Arg Leu Ile
65                  70                  75                  80

Thr Ala Asn Pro Ile Val Thr Asp Lys Glu Lys Pro Val Asn Ile Glu
                85                  90                  95

Thr Glu Pro Pro Phe Gly Glu Ser Tyr Ile Ile Val Gly Ala Gly Glu
            100                 105                 110

Lys Ala Leu Lys Leu Ser Trp Phe Arg Arg Asp Lys Arg Ser Val Ala
        115                 120                 125

Leu Ala Pro His Val Gly Leu Gly Leu Glu Thr Arg Thr Glu Thr Trp
    130                 135                 140

Met Ser Ser Glu Gly Ala Trp Lys Gln Ile Gln Lys Val Glu Thr Trp
145                 150                 155                 160

Ala Leu Arg His Pro Arg Arg Asp Lys Arg Asp Lys Leu Gln Leu Lys
                165                 170                 175

Gly Met Ser Tyr Ser Met Cys Thr Gly Lys Phe Lys Ile Val Lys Glu
            180                 185                 190

Ile Ala Glu Thr Gln His Gly Thr Ile Val Ile Arg Val Gln Tyr Glu
        195                 200                 205

Gly Asp Gly Ser Pro Cys Lys Ile Pro Phe Glu Ile Thr Asp Leu Glu
    210                 215                 220

Lys Arg His Val Leu Gly Arg Leu Ile Thr Val Asn Pro Ile Val Thr
225                 230                 235                 240

Glu Lys Asp Ser Pro Val Asn Ile Glu Ala Glu Pro Pro Phe Gly Asp
                245                 250                 255

Ser Tyr Ile Ile Val Gly Val Glu Pro Gly Gln Leu Lys Leu Asn Trp
            260                 265                 270

Phe Arg Arg Asp Lys Arg Ser Val Ala Leu Ala Pro His Val Gly Leu
        275                 280                 285

Gly Leu Glu Thr Arg Thr Glu Thr Trp Met Ser Ser Glu Gly Ala Trp
    290                 295                 300

Lys Gln Ile Gln Lys Val Glu Thr Trp Ala Leu Arg His Pro Arg Arg
305                 310                 315                 320

Asp Lys Arg Asp Lys Leu Lys Leu Lys Gly Met Ser Tyr Ala Met Cys
            325                 330                 335

Leu Asn Thr Phe Val Leu Lys Lys Glu Val Ser Glu Thr Gln His Gly
            340                 345                 350

Thr Ile Leu Ile Lys Val Glu Tyr Lys Gly Glu Asp Ala Pro Cys Lys
            355                 360                 365

Ile Pro Phe Ser Thr Glu Asp Gly Gln Gly Lys Ala His Asn Gly Arg
            370                 375             380

Leu Ile Thr Ala Asn Pro Val Val Thr Lys Lys Glu Pro Val Asn
385                 390                 395                 400

Ile Glu Ala Glu Pro Pro Phe Gly Glu Ser Asn Ile Val Ile Gly Ile
                405                 410                 415

Gly Asp Lys Ala Leu Lys Ile Asn Trp Tyr Arg Arg Asp Lys Arg Ser
            420                 425                 430

Val Ala Leu Ala Pro His Val Gly Leu Gly Leu Glu Thr Arg Thr Glu
            435                 440                 445

Thr Trp Met Ser Ser Glu Gly Ala Trp Lys Gln Ile Gln Lys Val Glu
            450                 455                 460

Thr Trp Ala Leu Arg His Pro Arg Arg Asp Lys Arg Glu Lys Leu Arg
465                 470                 475                 480

Ile Lys Gly Met Ser Tyr Thr Met Cys Ser Gly Lys Phe Ser Ile Asp
                485                 490                 495

Lys Glu Met Ala Glu Thr Gln His Gly Thr Thr Val Lys Val Lys
            500                 505                 510

Tyr Glu Gly Ala Gly Ala Pro Cys Lys Val Pro Ile Glu Ile Arg Asp
            515                 520                 525

Val Asn Lys Glu Lys Val Val Gly Arg Ile Ile Ser Ser Thr Pro Leu
530                 535                 540

Ala Glu Asn Thr Asn Ser Val Thr Asn Ile Glu Leu Glu Pro Pro Phe
545                 550                 555                 560

Gly Asp Ser Tyr Ile Val Ile Gly Val Gly Asn Ser Ala Leu Thr Leu
                565                 570                 575

His Trp Phe Arg Arg Asp Lys Arg Ser Val Ala Leu Ala Pro His Val
            580                 585                 590

Gly Leu Gly Leu Glu Thr Arg Thr Glu Thr Trp Met Ser Ser Glu Gly
            595                 600                 605

Ala Trp Lys Gln Ile Gln Lys Val Glu Thr Trp Ala Leu Arg His Pro
610                 615                 620

<210> SEQ ID NO 21
<211> LENGTH: 609
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 21

Met Leu Leu Ser Val Pro Leu Leu Gly Leu Leu Gly Leu Ala Val
1               5                   10                  15

Ala Asp Lys Leu Thr Leu Lys Gly Met Ser Tyr Val Met Cys Thr Gly
            20                  25                  30

Ser Phe Lys Leu Glu Lys Glu Val Ala Glu Thr Gln His Gly Thr Val
            35                  40                  45

Leu Val Gln Val Lys Tyr Glu Gly Thr Asp Ala Pro Cys Lys Ile Pro

-continued

```
             50                  55                  60
Phe Ser Thr Gln Asp Glu Lys Gly Val Thr Gln Asn Gly Arg Leu Ile
 65                  70                  75                  80

Thr Ala Asn Pro Ile Val Thr Asp Lys Glu Lys Pro Val Asn Ile Glu
                     85                  90                  95

Thr Glu Pro Pro Phe Gly Glu Ser Tyr Ile Ile Val Gly Ala Gly Glu
                100                 105                 110

Lys Ala Leu Lys Leu Ser Trp Phe Ser Val Ala Leu Ala Pro His Val
            115                 120                 125

Gly Leu Gly Leu Glu Thr Arg Thr Glu Thr Trp Met Ser Ser Glu Gly
        130                 135                 140

Ala Trp Lys Gln Ile Gln Lys Val Glu Thr Trp Ala Leu Arg His Pro
145                 150                 155                 160

Arg Arg Asp Lys Arg Asp Lys Leu Gln Leu Lys Gly Met Ser Tyr Ser
                165                 170                 175

Met Cys Thr Gly Lys Phe Lys Ile Val Lys Glu Ile Ala Glu Thr Gln
                180                 185                 190

His Gly Thr Ile Val Ile Arg Val Gln Tyr Glu Gly Asp Gly Ser Pro
            195                 200                 205

Cys Lys Ile Pro Phe Glu Ile Thr Asp Leu Glu Lys Arg His Val Leu
        210                 215                 220

Gly Arg Leu Ile Thr Val Asn Pro Ile Val Thr Glu Lys Asp Ser Pro
225                 230                 235                 240

Val Asn Ile Glu Ala Glu Pro Pro Phe Gly Asp Ser Tyr Ile Ile Val
                245                 250                 255

Gly Val Glu Pro Gly Gln Leu Lys Leu Asn Trp Phe Ser Val Ala Leu
                260                 265                 270

Ala Pro His Val Gly Leu Gly Leu Glu Thr Arg Thr Glu Thr Trp Met
            275                 280                 285

Ser Ser Glu Gly Ala Trp Lys Gln Ile Gln Lys Val Glu Thr Trp Ala
        290                 295                 300

Leu Arg His Pro Arg Arg Asp Lys Arg Asp Lys Leu Lys Leu Lys Gly
305                 310                 315                 320

Met Ser Tyr Ala Met Cys Leu Asn Thr Phe Val Leu Lys Lys Glu Val
                325                 330                 335

Ser Glu Thr Gln His Gly Thr Ile Leu Ile Lys Val Glu Tyr Lys Gly
                340                 345                 350

Glu Asp Ala Pro Cys Lys Ile Pro Phe Ser Thr Glu Asp Gly Gln Gly
            355                 360                 365

Lys Ala His Asn Gly Arg Leu Ile Thr Ala Asn Pro Val Val Thr Lys
        370                 375                 380

Lys Glu Glu Pro Val Asn Ile Glu Ala Glu Pro Pro Phe Gly Glu Ser
385                 390                 395                 400

Asn Ile Val Ile Gly Ile Gly Asp Lys Ala Leu Lys Ile Asn Trp Tyr
                405                 410                 415

Ser Val Ala Leu Ala Pro His Val Gly Leu Gly Leu Glu Thr Arg Thr
                420                 425                 430

Glu Thr Trp Met Ser Ser Glu Gly Ala Trp Lys Gln Ile Gln Lys Val
            435                 440                 445

Glu Thr Trp Ala Leu Arg His Pro Arg Arg Asp Lys Arg Glu Lys Leu
        450                 455                 460

Arg Ile Lys Gly Met Ser Tyr Thr Met Cys Ser Gly Lys Phe Ser Ile
465                 470                 475                 480
```

Asp Lys Glu Met Ala Glu Thr Gln His Gly Thr Thr Val Val Lys Val
            485                 490                 495

Lys Tyr Glu Gly Ala Gly Ala Pro Cys Lys Val Pro Ile Glu Ile Arg
            500                 505                 510

Asp Val Asn Lys Glu Lys Val Val Gly Arg Ile Ile Ser Ser Thr Pro
            515                 520                 525

Leu Ala Glu Asn Thr Asn Ser Val Thr Asn Ile Glu Leu Glu Pro Pro
            530                 535                 540

Phe Gly Asp Ser Tyr Ile Val Ile Gly Val Gly Asn Ser Ala Leu Thr
545                 550                 555                 560

Leu His Trp Phe Arg Arg Asp Lys Arg Ser Val Ala Leu Ala Pro His
                565                 570                 575

Val Gly Leu Gly Leu Glu Thr Arg Thr Glu Thr Trp Met Ser Ser Glu
            580                 585                 590

Gly Ala Trp Lys Gln Ile Gln Lys Val Glu Trp Ala Leu Arg His
            595                 600                 605

Pro

<210> SEQ ID NO 22
<211> LENGTH: 624
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 22

Met Leu Leu Ser Val Pro Leu Leu Leu Gly Leu Leu Gly Leu Ala Val
1               5                   10                  15

Ala Asp Lys Leu Thr Leu Lys Gly Met Ser Tyr Val Met Cys Thr Gly
            20                  25                  30

Ser Phe Lys Leu Glu Lys Glu Val Ala Glu Thr Gln His Gly Thr Val
            35                  40                  45

Leu Val Gln Val Lys Tyr Glu Gly Thr Asp Ala Pro Cys Lys Ile Pro
        50                  55                  60

Phe Ser Thr Gln Asp Glu Lys Gly Val Thr Gln Asn Gly Arg Leu Ile
65              70                  75                  80

Thr Ala Asn Pro Ile Val Thr Asp Lys Glu Lys Pro Val Asn Ile Glu
            85                  90                  95

Thr Glu Pro Pro Phe Gly Glu Ser Tyr Ile Ile Val Gly Ala Gly Glu
            100                 105                 110

Lys Ala Leu Lys Leu Ser Trp Phe Arg Arg Asp Lys Arg Ser Val Ala
            115                 120                 125

Leu Ala Pro His Val Gly Leu Gly Leu Glu Thr Arg Thr Glu Thr Trp
        130                 135                 140

Met Ser Ser Glu Gly Ala Trp Lys Gln Ile Gln Lys Val Glu Thr Trp
145                 150                 155                 160

Ala Leu Arg His Pro Arg Arg Asp Lys Arg Asp Lys Leu Gln Leu Lys
                165                 170                 175

Gly Met Ser Tyr Ser Met Cys Thr Gly Lys Phe Lys Ile Val Lys Glu
            180                 185                 190

Ile Ala Glu Thr Gln His Gly Thr Ile Val Ile Arg Val Gln Tyr Glu
        195                 200                 205

Gly Asp Gly Ser Pro Cys Lys Ile Pro Phe Glu Ile Thr Asp Leu Glu
        210                 215                 220

```
Lys Arg His Val Leu Gly Arg Leu Ile Thr Val Asn Pro Ile Val Thr
225                 230                 235                 240

Glu Lys Asp Ser Pro Val Asn Ile Glu Ala Glu Pro Pro Phe Gly Asp
            245                 250                 255

Ser Tyr Ile Ile Val Gly Val Glu Pro Gly Gln Leu Lys Leu Asn Trp
                260                 265                 270

Phe Arg Arg Glu Lys Arg Ser Val Ala Leu Val Pro His Val Gly Met
            275                 280                 285

Gly Leu Glu Thr Arg Thr Glu Thr Trp Met Ser Ser Glu Gly Ala Trp
        290                 295                 300

Lys His Val Gln Arg Ile Glu Thr Trp Ile Leu Arg His Pro Arg Arg
305                 310                 315                 320

Asp Lys Arg Asp Lys Leu Lys Leu Lys Gly Met Ser Tyr Ala Met Cys
                325                 330                 335

Leu Asn Thr Phe Val Leu Lys Lys Glu Val Ser Glu Thr Gln His Gly
                340                 345                 350

Thr Ile Leu Ile Lys Val Glu Tyr Lys Gly Glu Asp Ala Pro Cys Lys
                355                 360                 365

Ile Pro Phe Ser Thr Glu Asp Gly Gln Gly Lys Ala His Asn Gly Arg
370                 375                 380

Leu Ile Thr Ala Asn Pro Val Val Thr Lys Lys Glu Glu Pro Val Asn
385                 390                 395                 400

Ile Glu Ala Glu Pro Pro Phe Gly Glu Ser Asn Ile Val Ile Gly Ile
                405                 410                 415

Gly Asp Lys Ala Leu Lys Ile Asn Trp Tyr Arg Arg Asp Lys Arg Ser
                420                 425                 430

Val Ala Leu Ala Pro His Val Gly Met Gly Leu Asp Thr Arg Thr Gln
                435                 440                 445

Thr Trp Met Ser Ala Glu Gly Ala Trp Arg Gln Val Glu Lys Val Glu
        450                 455                 460

Thr Trp Ala Leu Arg His Pro Arg Arg Asp Lys Arg Glu Lys Leu Arg
465                 470                 475                 480

Ile Lys Gly Met Ser Tyr Thr Met Cys Ser Gly Lys Phe Ser Ile Asp
                485                 490                 495

Lys Glu Met Ala Glu Thr Gln His Gly Thr Thr Val Val Lys Val Lys
            500                 505                 510

Tyr Glu Gly Ala Gly Ala Pro Cys Lys Val Pro Ile Glu Ile Arg Asp
        515                 520                 525

Val Asn Lys Glu Lys Val Val Gly Arg Ile Ile Ser Ser Thr Pro Leu
530                 535                 540

Ala Glu Asn Thr Asn Ser Val Thr Asn Ile Glu Leu Glu Pro Pro Phe
545                 550                 555                 560

Gly Asp Ser Tyr Ile Val Ile Gly Val Gly Asn Ser Ala Leu Thr Leu
                565                 570                 575

His Trp Phe Arg Arg Glu Lys Arg Ser Val Ala Leu Thr Pro His Ser
                580                 585                 590

Gly Met Gly Leu Glu Thr Arg Ala Glu Thr Trp Met Ser Ser Glu Gly
        595                 600                 605

Ala Trp Lys His Ala Gln Arg Val Glu Ser Trp Ile Leu Arg Asn Pro
610                 615                 620

<210> SEQ ID NO 23
<211> LENGTH: 489
```

<212> TYPE: PRT
<213> ORGANISM: Artificial Sequence
<220> FEATURE:
<223> OTHER INFORMATION: Description of Artificial Sequence: Synthetic fusion sequence comprising domain(s) of Flaviviridae strains

<400> SEQUENCE: 23

| | | | | | | | | | | | | | | | |
|---|---|---|---|---|---|---|---|---|---|---|---|---|---|---|---|
| Met | Leu | Leu | Ser | Val | Pro | Leu | Leu | Leu | Gly | Leu | Gly | Leu | Ala | Val | |
| 1 | | | | 5 | | | | | 10 | | | | | 15 | |
| Ala | Asp | Lys | Leu | Thr | Leu | Lys | Gly | Met | Ser | Tyr | Val | Met | Cys | Thr | Gly |
| | | | 20 | | | | | 25 | | | | | 30 | | |
| Ser | Phe | Lys | Leu | Glu | Lys | Glu | Val | Ala | Glu | Thr | Gln | His | Gly | Thr | Val |
| | | 35 | | | | | 40 | | | | | 45 | | | |
| Leu | Val | Gln | Val | Lys | Tyr | Glu | Gly | Thr | Asp | Ala | Pro | Cys | Lys | Ile | Pro |
| 50 | | | | | 55 | | | | | 60 | | | | | |
| Phe | Ser | Thr | Gln | Asp | Glu | Lys | Gly | Val | Thr | Gln | Asn | Gly | Arg | Leu | Ile |
| 65 | | | | 70 | | | | | 75 | | | | | 80 | |
| Thr | Ala | Asn | Pro | Ile | Val | Thr | Asp | Lys | Glu | Lys | Pro | Val | Asn | Ile | Glu |
| | | | | 85 | | | | | 90 | | | | | 95 | |
| Thr | Glu | Pro | Pro | Phe | Gly | Glu | Ser | Tyr | Ile | Ile | Val | Gly | Ala | Gly | Glu |
| | | | 100 | | | | | 105 | | | | | 110 | | |
| Lys | Ala | Leu | Lys | Leu | Ser | Trp | Phe | Arg | Arg | Asp | Lys | Arg | Asp | Lys | Leu |
| | | | 115 | | | | | 120 | | | | | 125 | | |
| Gln | Leu | Lys | Gly | Met | Ser | Tyr | Ser | Met | Cys | Thr | Gly | Lys | Phe | Lys | Ile |
| | | 130 | | | | | 135 | | | | | 140 | | | |
| Val | Lys | Glu | Ile | Ala | Glu | Thr | Gln | His | Gly | Thr | Ile | Val | Ile | Arg | Val |
| 145 | | | | | 150 | | | | | 155 | | | | | 160 |
| Gln | Tyr | Glu | Gly | Asp | Gly | Ser | Pro | Cys | Lys | Ile | Pro | Phe | Glu | Ile | Thr |
| | | | | 165 | | | | | 170 | | | | | 175 | |
| Asp | Leu | Glu | Lys | Arg | His | Val | Leu | Gly | Arg | Leu | Ile | Thr | Val | Asn | Pro |
| | | | 180 | | | | | 185 | | | | | 190 | | |
| Ile | Val | Thr | Glu | Lys | Asp | Ser | Pro | Val | Asn | Ile | Glu | Ala | Glu | Pro | Pro |
| | | | 195 | | | | | 200 | | | | | 205 | | |
| Phe | Gly | Asp | Ser | Tyr | Ile | Ile | Val | Gly | Val | Glu | Pro | Gly | Gln | Leu | Lys |
| | | 210 | | | | | 215 | | | | | 220 | | | |
| Leu | Asn | Trp | Phe | Arg | Arg | Asp | Lys | Arg | Asp | Lys | Leu | Lys | Leu | Lys | Gly |
| 225 | | | | | 230 | | | | | 235 | | | | | 240 |
| Met | Ser | Tyr | Ala | Met | Cys | Leu | Asn | Thr | Phe | Val | Leu | Lys | Lys | Glu | Val |
| | | | | 245 | | | | | 250 | | | | | 255 | |
| Ser | Glu | Thr | Gln | His | Gly | Thr | Ile | Leu | Ile | Lys | Val | Glu | Tyr | Lys | Gly |
| | | | | 260 | | | | | 265 | | | | | 270 | |
| Glu | Asp | Ala | Pro | Cys | Lys | Ile | Pro | Phe | Ser | Thr | Glu | Asp | Gly | Gln | Gly |
| | | | 275 | | | | | 280 | | | | | 285 | | |
| Lys | Ala | His | Asn | Gly | Arg | Leu | Ile | Thr | Ala | Asn | Pro | Val | Val | Thr | Lys |
| | | 290 | | | | | 295 | | | | | 300 | | | |
| Lys | Glu | Glu | Pro | Val | Asn | Ile | Glu | Ala | Glu | Pro | Pro | Phe | Gly | Glu | Ser |
| 305 | | | | | 310 | | | | | 315 | | | | | 320 |
| Asn | Ile | Val | Ile | Gly | Ile | Gly | Asp | Lys | Ala | Leu | Lys | Ile | Asn | Trp | Tyr |
| | | | | 325 | | | | | 330 | | | | | 335 | |
| Arg | Arg | Asp | Lys | Arg | Glu | Lys | Leu | Arg | Ile | Lys | Gly | Met | Ser | Tyr | Thr |
| | | | 340 | | | | | 345 | | | | | 350 | | |
| Met | Cys | Ser | Gly | Lys | Phe | Ser | Ile | Asp | Lys | Glu | Met | Ala | Glu | Thr | Gln |
| | | | 355 | | | | | 360 | | | | | 365 | | |
| His | Gly | Thr | Thr | Val | Val | Lys | Val | Lys | Tyr | Glu | Gly | Ala | Gly | Ala | Pro |
| | | 370 | | | | | 375 | | | | | 380 | | | |

```
Cys Lys Val Pro Ile Glu Ile Arg Asp Val Asn Lys Glu Lys Val Val
385                 390                 395                 400

Gly Arg Ile Ile Ser Ser Thr Pro Leu Ala Glu Asn Thr Asn Ser Val
            405                 410                 415

Thr Asn Ile Glu Leu Glu Pro Pro Phe Gly Asp Ser Tyr Ile Val Ile
        420                 425                 430

Gly Val Gly Asn Ser Ala Leu Thr Leu His Trp Phe Arg Arg Asp Lys
            435                 440                 445

Arg Ser Val Ala Leu Ala Pro His Val Gly Leu Gly Leu Glu Thr Arg
        450                 455                 460

Thr Glu Thr Trp Met Ser Ser Glu Gly Ala Trp Lys Gln Ile Gln Lys
465                 470                 475                 480

Val Glu Thr Trp Ala Leu Arg His Pro
                485
```

<210> SEQ ID NO 24
<211> LENGTH: 474
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 24

```
Met Leu Leu Ser Val Pro Leu Leu Leu Gly Leu Leu Gly Leu Ala Val
1               5                   10                  15

Ala Asp Lys Leu Thr Leu Lys Gly Met Ser Tyr Val Met Cys Thr Gly
            20                  25                  30

Ser Phe Lys Leu Glu Lys Glu Val Ala Glu Thr Gln His Gly Thr Val
        35                  40                  45

Leu Val Gln Val Lys Tyr Glu Gly Thr Asp Ala Pro Cys Lys Ile Pro
    50                  55                  60

Phe Ser Thr Gln Asp Glu Lys Gly Val Thr Gln Asn Gly Arg Leu Ile
65                  70                  75                  80

Thr Ala Asn Pro Ile Val Thr Asp Lys Glu Lys Pro Val Asn Ile Glu
                85                  90                  95

Thr Glu Pro Pro Phe Gly Glu Ser Tyr Ile Ile Val Gly Ala Gly Glu
            100                 105                 110

Lys Ala Leu Lys Leu Ser Trp Phe Asp Lys Leu Gln Leu Lys Gly Met
        115                 120                 125

Ser Tyr Ser Met Cys Thr Gly Lys Phe Lys Ile Val Lys Glu Ile Ala
    130                 135                 140

Glu Thr Gln His Gly Thr Ile Val Ile Arg Val Gln Tyr Glu Gly Asp
145                 150                 155                 160

Gly Ser Pro Cys Lys Ile Pro Phe Glu Ile Thr Asp Leu Glu Lys Arg
                165                 170                 175

His Val Leu Gly Arg Leu Ile Thr Val Asn Pro Ile Val Thr Glu Lys
            180                 185                 190

Asp Ser Pro Val Asn Ile Glu Ala Glu Pro Pro Phe Gly Asp Ser Tyr
        195                 200                 205

Ile Ile Val Gly Val Glu Pro Gly Gln Leu Lys Leu Asn Trp Phe Asp
    210                 215                 220

Lys Leu Lys Leu Lys Gly Met Ser Tyr Ala Met Cys Leu Asn Thr Phe
225                 230                 235                 240

Val Leu Lys Lys Glu Val Ser Glu Thr Gln His Gly Thr Ile Leu Ile
```

|     |     |     |     |     | 245 |     |     |     | 250 |     |     |     |     | 255 |
| --- | --- | --- | --- | --- | --- | --- | --- | --- | --- | --- | --- | --- | --- | --- |

Lys Val Glu Tyr Lys Gly Glu Asp Ala Pro Cys Lys Ile Pro Phe Ser
              260         265      270

Thr Glu Asp Gly Gln Gly Lys Ala His Asn Gly Arg Leu Ile Thr Ala
       275        280       285

Asn Pro Val Val Thr Lys Lys Glu Glu Pro Val Asn Ile Glu Ala Glu
290         295       300

Pro Pro Phe Gly Glu Ser Asn Ile Val Ile Gly Ile Gly Asp Lys Ala
305        310       315      320

Leu Lys Ile Asn Trp Tyr Glu Lys Leu Arg Ile Lys Gly Met Ser Tyr
       325       330      335

Thr Met Cys Ser Gly Lys Phe Ser Ile Asp Lys Glu Met Ala Glu Thr
      340       345      350

Gln His Gly Thr Thr Val Val Lys Val Lys Tyr Glu Gly Ala Gly Ala
     355       360      365

Pro Cys Lys Val Pro Ile Glu Ile Arg Asp Val Asn Lys Glu Lys Val
370        375       380

Val Gly Arg Ile Ile Ser Ser Thr Pro Leu Ala Glu Asn Thr Asn Ser
385        390       395      400

Val Thr Asn Ile Glu Leu Glu Pro Pro Phe Gly Asp Ser Tyr Ile Val
       405       410      415

Ile Gly Val Gly Asn Ser Ala Leu Thr Leu His Trp Phe Arg Arg Asp
     420       425      430

Lys Arg Ser Val Ala Leu Ala Pro His Val Gly Leu Gly Leu Glu Thr
     435       440      445

Arg Thr Glu Thr Trp Met Ser Ser Glu Gly Ala Trp Lys Gln Ile Gln
     450       455      460

Lys Val Glu Thr Trp Ala Leu Arg His Pro
465        470

```
<210> SEQ ID NO 25
<211> LENGTH: 1890
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 25
cgtacgatgc tccttccgt cccgttgcta ttaggactac tcgggttggc tgtcgccgat      60
aagctgactc tgaagggaat gtcatacgtt atgtgcacag ggagcttcaa gttggagaag    120
gaggtggcag agacccagca cggaacagtc ttggtgcagg tcaagtacga gggcacggac    180
gctccttgta agatcccatt ctcaacccag gatgagaagg cgtgacccca gaatggacgg    240
ctgatcacgg ctaatcccat cgtgactgat aaggagaagc cagtcaacat cgagacagag    300 ccaccccttcg gtgagtctta cataatagtc ggggccggag agaaggctct caagctgagt    360
tggttcaggc gggataagcg aagcgtcgca cttgccccac acgttggcct cggactcgag    420
acaagaacag agacctggat gagcagcgag ggagcctgga agcagattca gaaggttgag    480
acctgggctc tccggcaccc tcgccgtgat aagagagaca agctgcagct taaggggatg    540
agttattcca tgtgcacagg caagttcaag attgtcaagg agatagcaga gactcagcac    600
ggaaccatag tgatcagagt tcagtacgag ggagacggat ccccatgcaa gattccgttt    660
gagattaccg acctggagaa gcgccacgtg ctggggagac tcattactgt gaacccaatc    720
```

| | |
|---|---|
| gtgactgaga aggattctcc cgtcaatatc gaggctgagc caccattcgg agattcttat | 780 |
| ataatcgttg gtgtagagcc tggccagttg aagttgaatt ggtttaggcg ggataagagg | 840 |
| agcgtggctc tcgctccaca tgttggcctg ggcctggaga cccgaacaga dacgtggatg | 900 |
| agctccgaag gtgcctggaa gcagattcag aaggttgaga cctgggccct gcgacaccct | 960 |
| agacgggata agcgcgataa gctgaagctt aagggtatgt cctacgcaat gtgcctgaac | 1020 |
| acgttcgtgc tgaagaagga ggtttcgag acccagcacg ggacaattct cattaaggtg | 1080 |
| gagtacaagg gcgaggacgc gccctgcaag atcccgttca gtactgaaga tggacagggc | 1140 |
| aaggctcaca atgggcgact cattactgct aatccagtgg tgaccaagaa ggaagagcca | 1200 |
| gtgaatatag aggcagagcc accatttgga gagagcaaca tcgtgatagg tatcggcgat | 1260 |
| aaggcactga agatcaactg gtatcgccgc gacaagcgat ccgtggcatt ggcgcctcat | 1320 |
| gtgggcctgg gtctagagac ccgcacagag acgtggatga gtagcgaagg cgcgtggaag | 1380 |
| cagatccaga aggtcgagac ttgggcactg cggcaccctc gacgtgacaa gcagagaag | 1440 |
| ctccgaatca agggaatgag ttacacaatg tgcagcggca agttctcaat gataaggag | 1500 |
| atggccgaga cccagcacgg cacaaccgtg gtcaaggtca agtacgaagg tgcgggcgct | 1560 |
| ccttgcaagg tcccaatcga gattagggat gtgaacaagg agaaggtcgt gggaagaatc | 1620 |
| attagttcca cgcctcttgc tgagaacact aatagtgtca ccaatatcga gctagagcca | 1680 |
| cccttcggag attcttacat tgtcattgga gttggcaatt ccgctcttac tctgcattgg | 1740 |
| tttaggagag ataagagaag cgtggccctg gcaccacacg tgggattagg gctggagaca | 1800 |
| cgaaccgaga cctggatgag cagcgaagga gcctggaagc agattcagaa ggtcgagact | 1860 |
| tgggccctca gacacccttg atgagcgcgc | 1890 |

<210> SEQ ID NO 26
<211> LENGTH: 1842
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 26

| | |
|---|---|
| cgtacgatgc tgttgagcgt gccattattg ctggggctgc tgggtctggc tgtggccgac | 60 |
| aagcttaccc tgaagggtat gagctacgtg atgtgcactg gttcgttcaa gctagagaag | 120 |
| gaggtggcag agacccagca tggaactgtg ttagtacaag ttaagtatga ggggaccgac | 180 |
| gcaccctgta agattccatt ctctacccaa gacgagaagg gcgtcacgca gaatggtcgc | 240 |
| ttgattacgg ctaatccaat agtgacggac aaggagaagc cagtgaatat cgagacagaa | 300 |
| cctccatttg gagaatccta cataatagtc ggggccggcg agaaggccct gaagttgtcc | 360 |
| tggttcagcg tggccctggc tccacacgtg ggcctgggcc tggagacccg aactgagact | 420 |
| tggatgtcgt ccgagggcgc ctggaagcag atccagaagg tagagacttg gcccctgcgc | 480 |
| catcctagga gagataagag ggacaagttg cagctcaagg gcatgtccta ctccatgtgt | 540 |
| acaggtaagt tcaagattgt gaaggagatt gctgagaccc agcacggcac catcgtaata | 600 |
| cgggtgcagt acgagggcga tggcagtcca tgtaagatac ctttcgagat cactgacctt | 660 |
| gagaagcgcc acgtgcttgg gcggctcatt accgtcaatc caatcgtgac tgagaaggat | 720 |
| agtccggtga atattgaggc tgagccgccg tttggggata gttatataat cgttggcgtg | 780 |
| gagcccggac aactcaagtt gaattggttc tctgtggcct tggcaccaca cgtggggctg | 840 |

```
ggcctggaga cacggaccga gacttggatg tcaagtgaag gagcctggaa gcagattcag    900
aaggtggaga cttgggccct tcggcaccct agacgtgata agcgcgacaa gctgaagctc    960
aagggaatgt cttacgccat gtgtctgaat actttcgtcc tgaagaagga ggtgtccgag   1020
actcagcatg ggactatcct gatcaaggtg gagtacaagg gtgaagacgc accatgtaag   1080
ataccattca gcacagagga cggtcagggc aaggctcata acgggcgcct tataactgcc   1140
aatccggttg tgaccaagaa ggaggagccc gtgaacatcg aggcagagcc accattcggc   1200
gagtccaaca tcgtgatagg aatcggtgat aaggccctca agattaattg gtattcagtg   1260
gccctggccc ctcacgtcgg actgggactc gagaccagga cagagacatg gatgtcttct   1320
gagggtgcat ggaagcagat acagaaggtt gagacctggg ccctcaggca cccacgtagg   1380
gacaagcggg agaagttgag gattaagggg atgtcgtaca ccatgtgcag cggcaagttc   1440
tccattgaca aggagatggc agagacgcag cacggaacaa cggtcgttaa ggtcaagtac   1500
gaaggagcgg gcgccccatg caaggtccca atcgagatta gggacgtgaa caaggagaag   1560
gttgtaggac ggattattag tagcacccca ctggcggaga atacgaatag tgtcacgaat   1620
atcgaactgg aaccacccttt cggcgatagc tacatcgtga ttggtgttgg caattccgca   1680
cttacactgc actggtttcg gagagacaag cgaagcgtgg ccctggcccc tcacgtggga   1740
cttggcctgg agaccgcac agagacttgg atgtcctctg aaggagcatg gaagcagatt   1800
cagaaggtgg agacttgggc attacgccac ccatgagcgc gc                      1842
```

<210> SEQ ID NO 27
<211> LENGTH: 1890
<212> TYPE: DNA
<213> ORGANISM: Artificial Sequence
<220> FEATURE:
<223> OTHER INFORMATION: Description of Artificial Sequence: Synthetic fusion sequence comprising domain(s) of Flaviviridae strains

<400> SEQUENCE: 27

```
cgtacgatgc tgctatctgt gccactgctc ctgggactgc tggggctggc cgtggctgac     60
aagttgacgc ttaaggggat gtcctacgta atgtgcacag gatcattcaa gctagagaag    120
gaagttgcag agacgcagca cggcaccgtg ctggttcagg tgaagtacga gggcactgat    180
gcaccctgca agatcccatt cagtactcag gacgagaagg gagtcacgca gaatgggagg    240
ctcatcacgg ccaacccaat tgttaccgac aaggagaagc cgttaatat agagactgaa    300 ccgcccttcg gggagtcata cattattgtg ggcgcagggg agaaggctct gaagctttcc    360
tggttccgta gggataagcg cagcgtggcg ctagcccctc atgtgggtct cgggctggag    420
actcgcaccg agacatggat gtcatccgag ggtgcgtgga gcagatcca aaggttgag     480 acatgggcac ttcgccaccc acggcgcgac aagcgtgaca agcttcagct gaaggggatg    540
tcttatagca tgtgcacagg caagttcaag atcgtcaagg atagcagag acacagcat    600 ggcacaatag tcatacgggt gcaatatgag ggagatggct ctccgtgtaa gatacctttc    660
gagatcaccg atctggagaa gcggcacgtc ctcgggagac taattacggt gaacccaatt    720
gtgacagaga aggatagccc agttaatatt gaggccgaac cacccttcgg agacagctac    780
attatcgtag gagtcgagcc agggcagctg aagctgaact ggttccgcag ggagaagcgt    840
tccgtcgctc ttgttccaca tgtgggaatg ggcctggaga cccgcaccga cacatggatg    900
agcagcgagg gtgcctggaa gcacgtacag agaattgaga cttggatctt aaggcatcct    960
cggcgggata agcgcgacaa gttgaagctg aagggaatgt cttacgcaat gtgtttgaac   1020
```

```
acttccgtcc tgaagaagga ggtgtcagag acccagcacg gaactatact tattaaggtt    1080
gagtacaagg gagaagacgc tccttgcaag atcccattct caactgaaga tgggcagggc    1140
aaggcacaca acggaaggct catcacagct aacccagtgg ttaccaagaa ggaggagccc    1200
gtgaacatcg aagccgagcc gcccttcgga gagagcaaca tagtgatcgg tattgggat     1260 aaggctctga agatcaattg gtatcgccgg gacaagagaa gtgtggccct ggccccacat    1320
gtcggcatgg gcttggacac acggacacag acatggatgt ccgctgaagg agcctggagg    1380
caggtggaga aggtcgagac ctgggcgctg cgccacccgc gtcgagacaa gagagagaag    1440
ttaagaatca agggtatgtc ctacacgatg tgttccggta agttctccat agacaaggag    1500
atggctgaga cccagcacgg cactacggtg gtcaaggtga agtatgaggg agccggcgca    1560
ccttgcaagg tgccgatcga gatccgcgac gtcaacaagg agaaggtggt cgggcgcatc    1620
atttccagta ccccattagc tgagaatact aatagcgtga ctaatattga gttggaacca    1680
cccttcggag actcttacat cgttatcggg gtgggcaact cagctcttac acttcactgg    1740
ttccgcaggg agaagagatc agtggcccta accctcact caggcatggg cctggagact     1800
cgggccgaga cctggatgag cagcgagggt gcctggaagc acgcccagcg agtggaatcg    1860
tggattctta ggaatccatg atgagcgcgc                                      1890

<210> SEQ ID NO 28
<211> LENGTH: 1482
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 28
cgtacgatgc tgttatctgt acctctcctg ctcggcctcc ttggactggc agttgcagat     60
aagcttacac tcaagggaat gtcctatgtg atgtgtaccg ggtccttcaa gttggagaag    120
gaggtagctg agacgcagca tggcacagtg ctggtgcagg ttaagtatga aggaactgat    180
gctccgtgta agatcccgtt cagtactcag gatgagaagg gtgtgaccca gaatggccgc    240
ttaattacag ccaaccctat cgtaactgac aaggagaagc ctgtgaacat cgagactgaa    300
ccacccttcg gtgagagtta tataatagtt ggcgccggag agaaggccct caagcttagc    360
tggtttcggc gcgacaagcg agataagctc aacttaagg gaatgtcata ctcaatgtgc    420
acaggtaagt tcaagatagt gaaggagata gccgagaccc agcatggcac catcgtgatc    480
agagtccaat atgaaggaga cgggtctcct tgtaagatcc cattcgagat aacagacttg    540
gagaagaggc acgtgctggg acgtctgata acagttaatc ccatagttac cgagaaggat    600
agccctgtta acattgaggc tgaacctccc ttcggagatt cctacattat tgtcggcgtg    660
gagccaggtc agctgaagct taactggttc agacgggaca agcgcgacaa gctgaagttg    720
aagggcatgt cctatgcaat gtgtctcaat actttcgttc tcaagaagga agtgagcgag    780
acacagcatg gcaccatatt aattaaggtt gagtacaagg gtgaggatgc tccttgcaag    840
attcctttca gcaccgagga tggacagggc aaggcccaca atggtcggct gatcaccgcc    900
aaccctgtgg taaccaagaa ggaagagccc gtcaacatag aagccgagcc gccgtttggc    960
gagtccaata tagtaatcgg catcggagat aaggccttga agattaattg gtacaggcgg    1020
gataagcgcg agaagttacg gattaagggt atgtcttaca ctatgtgtag cggtaagttt    1080
agcatcgaca aggagatggc agagacccag catggcacta ccgtggtcaa ggtgaagtac    1140
```

```
gaaggagctg agcaccatg  taaggtccct atcgagatcc gcgacgtgaa caaggagaag    1200
gtggtgggaa gaatcatctc ttccacacct ctggcagaga acacgaatag cgtgactaat    1260
atcgaacttg agcctccttt cggcgattcc tacatcgtta ttggcgtggg caactccgcc    1320
ctgacactgc attggtttag acgtgacaag cgtagcgtgg cccttgcacc acacgtgggc    1380
ctaggcctgg agacgcgtac agagacatgg atgagcagtg aaggagcctg gaagcagatt    1440
cagaaggtcg agacctgggc tctcagacat ccttgagcgc gc                        1482
```

<210> SEQ ID NO 29
<211> LENGTH: 1440
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae strains

<400> SEQUENCE: 29

```
cgtacgatgc tcctaagcgt tccactgctt ctgggactgc tgggtttggc cgttgccgac      60
aagctcacgc tcaaggggat gagctacgtc atgtgcacag gctcattcaa gttggagaag     120
gaagtcgccg agacgcagca cggaacagta ctcgtgcagg tcaagtatga gggcaccgac     180
gctccatgca agatcccgtt ctccacacag gacgagaagg gcgttactca gaacggaaga     240
ttaattactg ccaatcctat agtaacagac aaggagaagc tgtgaatat tgagactgag      300 cctcccttcg gtgaatccta catcattgta ggggctggcg agaaggcttt gaagctctcc     360
tggtttgata gctgcagct caagggaatg tcgtattcaa tgtgcactgg gaagttcaag     420
attgtgaagg agattgcaga gactcaacac ggcaccattg tgataagggt ccagtacgag     480
ggtgatgggt caccctgcaa gattcccttt gagatcacag accttgagaa gaggcacgta     540
cttgggcgat taattaccgt gaatcctatt gtgactgaga aggatagtcc cgtgaacatt     600
gaagctgagc ctcctttcgg agatagctac attatcgtgg gagtcgagcc tggccagttg     660
aagctcaact ggtttgataa gctgaagctc aagggcatgt cctacgctat gtgcttgaat     720
acatttgtgc tgaagaagga ggtgagtgag acccaacacg gaaccatcct gatcaaggtg     780
gagtacaagg gtgaagatgc accttgcaag atccctttct ccactgaaga cgggcagggc     840
aaggcccata tgggagact cataacagct aatccagtgg tcaccaagaa ggaagaacca     900
gtcaacatcg aggcggagcc accatttggg gagagtaaca tcgtgatcgg tattggcgat     960
aaggccctga agattaactg gtatgagaag ttgagaatta aggggatgag ctataccatg    1020
tgctcaggta agttcagcat cgataaggag atggccgaga cacagcacgg gaccacagtt    1080
gtgaaggtga agtacgaggg cgctgggggcc ccatgcaagg tgcctatcga gattcgcgac    1140
gtgaacaagg agaaggtcgt ggggcgaatc atctcatcca ccctctcgc agagaacacg     1200 aactctgtga ccaatattga gctggaacca ccttccgag actcatatat cgtcataggc     1260
gtcggcaatt cagcttttgac attgcactgg ttcagacggg acaagcggtc cgttgccctg    1320
gctccacacg tcggcctggg cctttgagact aggacggaga cctggatgtc ctccgagggc    1380
gcctggaagc agatccagaa ggtggagacc tgggccctgc gccacccctg ataggcgcgc    1440
```

<210> SEQ ID NO 30
<211> LENGTH: 40
<212> TYPE: PRT
<213> ORGANISM: Flavivirus sp.

<400> SEQUENCE: 30

```
Ser Val Ala Leu Ala Pro His Val Gly Leu Glu Thr Arg Thr
1               5                   10                  15

Glu Thr Trp Met Ser Ser Glu Gly Ala Trp Lys Gln Ile Gln Lys Val
            20                  25                  30

Glu Thr Trp Ala Leu Arg His Pro
        35                  40

<210> SEQ ID NO 31
<211> LENGTH: 40
<212> TYPE: PRT
<213> ORGANISM: Flavivirus sp.

<400> SEQUENCE: 31

Ser Val Ala Leu Ala Pro His Val Gly Met Gly Leu Asp Thr Arg Thr
1               5                   10                  15

Gln Thr Trp Met Ser Ala Glu Gly Ala Trp Arg Gln Val Glu Lys Val
            20                  25                  30

Glu Thr Trp Ala Leu Arg His Pro
        35                  40

<210> SEQ ID NO 32
<211> LENGTH: 40
<212> TYPE: PRT
<213> ORGANISM: Flavivirus sp

```
<220> FEATURE:
<223> OTHER INFORMATION: Description of Artificial Sequence: Synthetic
      pentapeptide binding segment

<400> SEQUENCE: 35

Arg Arg Glu Lys Arg
1               5
```

CHIMERIC POLY PEPTIDES AND THE THERAPEUTIC USE THEREOF AGAINST A FLAVIVIRIDAE INFECTION

This application is a continuation of application Ser. No. 11/917,907 (now U.S. Pat. No. 8,337,857 B2), which is the national stage of International Application No. PCT/FR2006/001396, filed Jun. 20, 2006, which claims priority to Canadian Application No. 2508266, filed Jun. 20, 2005.

SEQUENCE LISTING

The instant application contains a Sequence Listing which has been submitted in ASCII format via EFS-Web and is hereby incorporated by reference in its entirety. Said ASCII copy, created on Apr. 20, 2012, is named DI20521A.txt and is 85,853 bytes in size.

FIELD OF THE INVENTION

The present invention relates to the construction of a chimeric polypeptide for use in the prevention or treatment of a Flaviviridae infection. The present invention also relates to the use of the chimeric polypeptide in the production of recombinant viral vectors, such as a live measles viral vector to act as a vaccine.

BRIEF DESCRIPTION OF THE PRIOR ART

Flaviviruses (the Flaviviridae family) are envelope viruses the genome of which is a RNA molecule with a positive polarity. The flavivirion is composed of three structural proteins designated C (core protein), M (membrane protein) and E (envelope protein). The E protein, which is exposed on the virus surface, is responsible for the principal biological functions of the virion, including attachment of the virus and specific membrane fusion. Translation of genomic RNA produces a precursor polyprotein which is simultaneously cleaved by cellular and viral proteases to generate individual viral proteins: three structural proteins C, prM (the glycosylated precursor of the M protein), E, and seven non-structural proteins NS1 to NS5. Replication of flaviviruses occurs in the cytoplasm of infected cells. Flaviviruses have complex natural transmission cycles which involve several natural hosts (mainly mammals and birds) and vectors, the latter being hematophage arthropods such as ticks and mosquitoes. These viruses are the principal cause of severe human diseases such as hemorrhagic manifestations or meningo-encephalitic syndromes. The dengue virus (DEN) is one of the two major flaviviruses known to be the cause of severe hemorrhagic diseases across the world.

Dengue is an emerging disease and a bane to public health. Development of live-attenuated vaccine candidates against the four serotypes of the dengue virus has been carried out for more than 50 years. The search for a vaccine is hindered by the absence of an animal model which mimics the disease caused by the dengue virus, namely the hemorrhagic fever of dengue and the shock syndrome associated therewith. Vaccine effectiveness can be evaluated in the mouse using a neurovirulent strain of DEN virus adapted to the mouse, which kills adult animals after intracerebral inoculation. However, studies based on that type of murine model do not reflect the activity of the dengue virus in man. In the monkey, protection can only be demonstrated by measuring the reduction in viremia after an experimental infectious challenge. Thus, the ultimate test for a vaccine against dengue must be based on clinical trials carried out in man. The majority of attenuated vaccine candidates which have been developed over the last 50 years have been either too reactogenic or insufficiently immunogenic in clinical trials. Several attenuated tetravalent candidates are currently in phase I or II clinical trials. The difficulty in the development of this type of live-attenuated tetravalent vaccines appears to be in obtaining a balanced mixture of four valencies in order to generate protective immunity against the four serotypes.

Various live chimeric vaccine candidates are also being developed. They are based on the exchange of homologous structural genes between different flaviviruses. Several types of intertype chimeric viruses have been constructed and tested in the mouse or monkey. Chimeric viruses have been constructed with Chimerivax® techniques based on the yellow fever vaccinal virus (YF-17D). Tetravalent mixtures of those YF-17D/DEN chimeras have been tested in the rhesus monkey. Here again, the balance between the four chimeric viruses is difficult to obtain for uniform immunization. A phase 1111 clinical test is currently being prepared to test a chimerivax-dengue 2 vaccine. Other approaches include subunit candidate vaccines produced from an expression vector, and naked DNA type candidates which are in pre-clinical development. Thus, the development of a tetravalent vaccine against the dengue virus is still an unresolved problem, one of the most important on the list of the World Health Organization.

Thus, there is a need to develop novel effective vaccine candidates which are easy to produce and to formulate, for the prevention or treatment of an infection by a virus of the Flaviviridae family such as the dengue virus.

SUMMARY OF THE INVENTION

The present invention relates to a chimeric polypeptide and its applications in the prevention or treatment of an infection by Flaviviridae.

More particularly, an object of the present invention is a chimeric polypeptide comprising a peptide of a subdomain the E protein of Flaviviridae bound to a peptide of a subdomain of the Membrane M protein of Flaviviridae.

An object of the present invention is also an isolated or purified polynucleotide coding for a chimeric polypeptide of the invention.

An object of the present invention is also a recombinant measles viral vector into the genome of which a polynucleotide of the invention has been inserted.

An object of the invention also pertains to purified monoclonal or polyclonal antibodies specifically recognizing at least one polynucleotide as defined above and/or the chimeric polypeptide of the invention.

The invention also relates to the use of a viral vector of the invention for the preparation of an immunogenic composition intended for the prevention or treatment of a Flaviviridae infection in a sensitive species.

The present invention also relates to cloning or expression vectors comprising a polynucleotide of the invention.

Another object of the present invention is to provide an immunogenic composition intended for the prevention and/or treatment of a Flaviviridae infection in a sensitive species, characterized in that it comprises at least one of the following elements:
 a chimeric polypeptide as defined above;
 a polynucleotide according to the invention;
 a recombinant viral vector according to the invention;
 an antibody according to the invention; and
 a cloning and/or expression vector according to the invention.

The present invention also proposes a method for preventing and/or treating a Flaviviridae infection in a sensitive species, comprising administering a pharmaceutically effective amount of at least one of the following elements:
- a chimeric polypeptide as defined above;
- a polynucleotide according to the invention;
- a recombinant viral vector according to the invention;
- an antibody according to the invention; and
- a cloning and/or expression vector according to the invention.

BRIEF DESCRIPTION OF THE FIGURES

FIG. 1 shows the 384 nucleotide (nt) sequence coding for the [EDIII]$_{DV-1}$ domain of the FGA/89 viral strain fused via the Arg-Ser dipeptide to the signal peptide of calreticulin (ssCRT) flanked by the two BsiWI (5') and BssHII (3') sites necessary for insertion into the MV$_{Schw}$ vector;

FIG. 2 shows the 516 nucleotide (nt) sequence coding for the [EDIII+M$^{1-40}$]$_{DV-1}$ fusion protein of the FGA/89 viral strain fused via the Arg-Ser dipeptide to the signal peptide of calreticulin (ssCRT) flanked by the two BsiWI (5') and BssHII (3') sites necessary for insertion into the MV$_{Schw}$ vector;

FIG. 3 shows Vero cells infected with recombinant measles viral vectors according to the invention. Multiplicity of infection 10 TCIP50/cell for 30 h. Immunofluorescence carried out with a specific anti-DV-1 HMAF antibody;

FIG. 6 shows a nucleotide sequence coding for a chimeric polypeptide according to a preferred mode of the invention;

FIG. 7 shows an amino acid sequence of a chimeric polypeptide according to a preferred mode of the invention and the nucleotide sequence coding for it;

FIG. 8 shows an amino acid sequence of a dimer of the ectodomain III (EDIII) according to a preferred mode of the invention, and the nucleotide sequence coding for it;

FIG. 9 shows an amino acid sequence of a dimer of the ectodomain III (EDIII) according to a preferred mode of the invention, and the nucleotide sequence coding for it;

FIG. 10 shows an amino acid sequence of a chimeric polypeptide according to a preferred mode of the invention, and the nucleotide sequence coding for it;

FIG. 11 shows an amino acid sequence of the ectodomain III (EDIII) according to a preferred mode of the invention, and the nucleotide sequence coding for it;

FIG. 12 shows an amino acid sequence of a dimer of the ectodomain III (EDIII) according to a preferred mode of the invention, and the nucleotide sequence coding for it;

FIG. 13 shows a nucleic acid sequence coding for a peptide of the ectodomain III (EDIII) peptide according to a preferred mode of the invention;

FIG. 14 shows a nucleotide sequence coding for a chimeric polypeptide according to a preferred mode of the invention;

FIGS. 15 to 19 show an amino acid sequence of chimeric polypeptides according to a preferred mode of the invention;

FIGS. 20 to 24 show a nucleotide sequence coding respectively for the chimeric polypeptides of FIGS. 15 to 19;

FIGS. 25 to 29 respectively show a representative diagram of the chimeric polypeptides of FIGS. 15 to 19;

FIG. 30 shows the peptide sequence of the apoptoM sequence of four serotypes of the dengue virus used in the construction of a chimeric precursor according to the invention.

DETAILED DESCRIPTION OF THE INVENTION

Figure 4:
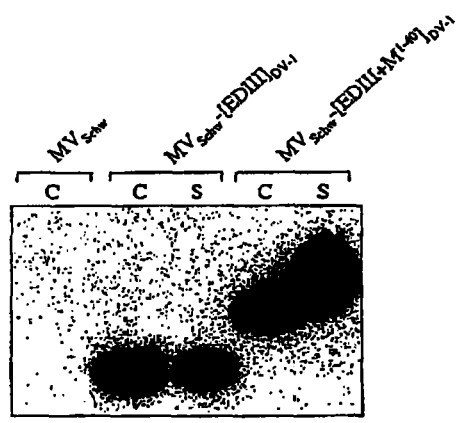
FIG. 4 shows the expression and secretion of the [EDIII]$_{DV-1}$ and [EDIII+M$^{1-40}$]$_{DV-1}$ antigenic domains in cytoplasmatic lysates (C) and supernatants (S) from Vero cells infected with recombined MVSchw-DV-1 viruses.

The originality of the present invention is based on the construction of a chimeric polypeptide and its applications in the prevention or treatment of an Flaviviridae infection. The term "Flaviviridae" means a virus selected from the group constituted by the West Nile virus, dengue virus, Japanese encephalitis virus and yellow fever virus.

1. Polypeptide and Polynucleotide

In a first aspect, the present invention relates to a chimeric polypeptide comprising a peptide of a subdomain of the E protein of Flaviviridae linked to a peptide of a subdomain of the membrane M protein of Flaviviridae. The invention also pertains to a polypeptide which consists of said peptides.

The term "polypeptide" as used in the present invention means both proteins and peptides. By "chimeric polypeptide" it is meant any protein or peptide comprising sub-portions of different origins, for example a polypeptide A deriving from a first species and a polypeptide (protein or peptide) deriving from a second species. A protein or peptide is also considered to be a chimeric polypeptide if it includes sub-portions deriving from different proteins or peptides from the same species, or even from the same protein or peptide from different species.

Preferably, the peptide of a subdomain of the E protein consists of the ectodomain III comprising an amino acid sequence as defined in any one of the following sequences:
- amino acids 19 to 120 of SEQ ID NO: 1;
- amino acids 19 to 119 of SEQ ID NO: 3;
- amino acids 21 to 123 of SEQ ID NO: 6;
- amino acids 21 to 121 of SEQ ID NO: 12; and
- amino acids 21 to 123 of SEQ ID NO: 14.

More particularly, the peptide of a subdomain of the E protein consists of a dimer of the ectodomain III of the dengue 1, 2, 3 or 4 virus comprising an amino acid sequence as defined in any one of the following sequences:
- amino acids 21 to 262 of SEQ ID NO: 8; and
- amino acids 21 to 262 of SEQ ID NO: 10;

or a tetramer of the ectodomain III of the dengue 1, 2, 3, 4 virus comprising a sequence ranging from amino acid 21 to 494 of SEQ ID NO: 16 or ranging from amino acid 18 to 429 of SEQ ID NO: 24.

Regarding the peptide of a subdomain of the M protein, this in particular consists of the ectodomain 1-40 comprising an amino acid sequence ranging from position 123 to 170 of SEQ ID NO: 3 or in the apoptoM sequence comprising an amino acid sequence ranging from position 154 to 170 of SEQ ID NO: 3 or ranging from position 122 to 132 of SEQ ID NO: 12.

Highly preferably, the chimeric polypeptide of the invention comprises an amino acid sequence as defined in any one of the following sequences:
a) amino acids 19 to 162 of SEQ ID NO: 3;
b) amino acids 21 to 168 of SEQ ID NO: 6;
c) amino acids 21 to 132 of SEQ ID NO: 12;
d) amino acids 18 to 624 of SEQ ID NO: 20;
e) amino acids 18 to 609 of SEQ ID NO: 21;
f) amino acids 18 to 624 of SEQ ID NO: 22;
g) amino acids 18 to 489 of SEQ ID NO: 23; and
h) amino acids 21 to 474 of SEQ ID NO: 24.

The invention also relates to polypeptides (and fragments thereof) which are coded by the nucleotide sequences mentioned below.

Highly preferably, the polypeptide of the invention has a percentage identity of at least 80% after optimum alignment with a sequence as defined in any one of amino acid sequences a) to h) defined above, preferably at least 90%, more preferably at least 98% and still more preferably at least 100%.

In a connected aspect, the invention relates to an isolated or purified polynucleotide coding for a chimeric polypeptide as defined above.

By "isolated or purified", it is meant molecules which have been altered by man from their native state, i.e. if such molecules exist in nature, they have been changed and/or removed from their initial environment. As an example, a polynucleotide or a polypeptide naturally present and found in the biological environment of a living organism which naturally expresses it is not "isolated" in this context. However, the same polynucleotide or polypeptide when separated from its natural environment and/or obtained by cloning, amplification and/or chemical synthesis is considered in the present invention to be "isolated". Further, a polynucleotide or polypeptide which is introduced into an organism by transformation, gene manipulation or any other recombination method is "isolated" even if it is present in said organism.

By the terms "nucleotide sequence", "nucleic acid", "nucleic sequence or nucleic acid sequence", "polynucleotide", oligo nucleotide", "polynucleotide sequence", which will be used indiscriminately in the present description, it is meant a precise chain of nucleotides, which may or may not be modified, which allows to define a fragment or a region of a nucleic acid, which may or may not comprise non-natural nucleotides and which can correspond both to a double-stranded DNA, a single-stranded DNA or to transcription products of said DNAs. Thus, the nucleic sequences of the invention also encompass PNAs (peptide nucleic acid) or the like. The polynucleotide fragments of the invention comprise at least 15 consecutive nucleotides. Preferably, they comprise at least 20 consecutive nucleotides and more preferably they comprise at least 30 consecutive nucleotides.

The invention also pertains to fragments of polynucleotides, which consist of fragments of 15, 20 or 30 successive nucleotides.

Any polynucleotide which has been chemically, enzymatically or metabolically modified but which has retained the biochemical properties of the original chimeric polypeptide is included within the scope of the present invention.

In a preferred embodiment, the polynucleotide of the present invention, when it codes for a chimeric polypeptide of the invention, advantageously comprises a nucleotide sequence as defined in any one of the following sequences:

a) nucleotides 7 to 492 of SEQ ID NO: 4;
b) SEQ ID NO: 5;
c) Nucleotides 7 to 504 of SEQ ID NO: 7;
d) Nucleotides 7 to 504 of SEQ ID NO: 13; and
e) SEQ ID NOs: 25 to 29.

Highly preferably, the polynucleotide of the invention has a percentage identity of at least 80% after optimum alignment with a sequence as defined in any one of the nucleotide sequences a) to e) defined above, preferably at least 90%, more preferably at least 98% and most preferably at least 100% identity.

The term "percentage identity" between two nucleic acid or amino acid sequences as used in the present invention means a percentage of identical nucleotides or amino acid residues between the two sequences to be compared, obtained after best alignment, that percentage being purely statistical and the differences between the two sequences being randomly distributed and over their entire length. By "best alignment" or "optimum alignment", it is meant the alignment at which the percentage identity determined as below is the highest. Sequence comparisons between two nucleic acid or amino acid sequences are traditionally carried out by comparing these sequences after having aligned them in an optimum manner, said comparison being carried out using comparison segments or windows to identify and compare local regions with sequence similarity. The optimum sequence alignment for comparison may be carried out manually or using a Smith and Waterman (1981) local homology algorithm, using the Neddleman and Wunsch (1970) local homology algorithm, using the Pearson and Lipman (1988) sequence similarity search method, or using software employing these algorithms (GAP, BESTFIT, BLAST P, BLAST N, FASTA and TFASTA in the Wisconsin Genetics Software Package, Genetics Computer Group, 575 Science Dr, Madison, Wis.). To obtain an optimal alignment, the BLAST program is preferably used, with the BLOSUM 62 matrix. It is also possible to use PAM or PAM250 matrices.

The percentage identity between two nucleic acid or amino acid sequences is determined by comparing these two sequences aligned in an optimum manner, the nucleic acid or amino acid sequence to be compared possibly comprising additions or deletions compared with the reference sequence for optimum alignment between these two sequences. The percentage identity is calculated by determining the number of identical positions for which the nucleotide or amino acid residue is identical between the two sequences, dividing this number of identical positions by the total number of compared positions and multiplying the result obtained by 100 to obtain the percentage identity between these two sequences.

The term "nucleic sequences having a percentage identity of at least 80%, preferably at least 90%, more preferably at least 98% after optimum alignment with a reference sequence", is intended to designate nucleic sequences having, with respect to the reference nucleic acid, certain modifications, in particular a deletion, truncation, extension, chimeric fusion, and/or a substitution, in particular a point substitution, and for which the nucleic sequence has at least 80%, preferably at least 90%, more preferably at least 98% identity after optimum alignment with the reference nucleic sequence. Preferably, the specific hybridization conditions or high stringency conditions will be such that they ensure at least 80%, preferably at least 90%, more preferably at least 98% identity after optimum alignment between one of the two sequences and the complementary sequence of the other.

A hybridization under high stringency conditions means that the temperature and ionic strength conditions are selected so that they can maintain the hybridization between two complementary nucleic acid fragments. By way of illustration, the highly stringent conditions for the hybridization step with the aim of defining the nucleotide sequences described above are advantageously as follows.

DNA-DNA or DNA-RNA hybridization is carried out in two steps: (1) pre-hybridization at 42° C. for 3 hours in a phosphate buffer (20 mM, ph 7.5) containing 5×SSC (1×SSC corresponds to a solution of 0.15 M NaCl+0.015 M of sodium citrate), 50% formamide, 7% sodium dodecyl sulphate (SDS), 10×Denhardt's solution, 5% dextran sulphate and 1% salmon sperm DNA; (2) hybridization proper for 20 hours at a temperature depending on the probe size (i.e.: 42° C. for a probe size>100 nucleotides), followed by 2 washings of 20 minutes at 20° C. in 2×SSC+2% SDS, 1 washing of 20 minutes at 20° C. in 0.1×SSC+0.1% SDS. The final washing is carried out in 0.1×SSC+0.1% SDS for 30 minutes at 60° C. for a probe size>100 nucleotides. The high stringency hybridization conditions described above for a polynucleotide of a defined size may be adapted by the skilled person for larger or smaller oligonucleotides, as discussed by Sambrook et al, 1989.

The polypeptides and polynucleotides of the present invention may be prepared using any appropriate process. They may in particular be obtained by chemical synthesis, but it is also possible to obtain them via a biological route pathway, especially using different vectors in appropriate cell cultures. The peptides of the present invention may, if necessary, be in the deglycosylated or glycosylated form. A person skilled in the field of the invention will be able to obtain different polynucleotides/polypeptides and will also be able to determine which of the polynucleotides/polypeptides obtained have a suitable biological activity.

2. Recombinant Viral Vector

In a further aspect, the invention concerns a recombinant measles viral vector with a polynucleotide of the invention inserted into the genome thereof. Such vectors are prepared using methods which are routinely used by the skilled person and the resulting clones may be introduced into a suitable host using standard methods which are known to the skilled person.

In a preferred mode, the recombinant viral vector of the invention is advantageously a live measles (Schwarz strain) viral vector, such as those selected from the group of viral vectors constituted by those deposited at the CNCM under numbers 1-3440, 1-3442, 1-3452, 1-3453, I-3454, 1-3455, 1-3619, 1-3620, 1-3621, 1-3622 and 1-3623. The complete antigenome sequence of the measles Schwarz strain virus can, for example, be obtained from pTM plasmids of strains deposited under numbers 1-3440 and 1-3442.

The vector pTM-MVSchw2-[EDIII+M$^{1-40}$]WNV(IS-98-ST1) was deposited at the CNCM (Paris, France) on 26 May 2005 under number 1-3440.

This vector is a pTM plasmid containing the complete antigenome of the measles virus, Schwarz strain, and an additional expression unit placed between the P and M genes containing the sequence of the domain III of the envelope E protein of West Nile virus (WNV IS-98-ST1) fused to the sequence 1-40 of the membrane protein.

The vector may be cultivated in 100 μ/ml LB ampicillin medium after inoculating small colonies.

It is preserved long-term by freezing at −80° C.

The vector pTM-MVSchw2-[EDIII+ApoptoM]DV-1 (FGA89) was deposited at the CNCM (Paris, France) on 26 May 2005 under number 1-3442.

This vector is a pTM plasmid containing the complete antigenome of the measles virus, Schwarz strain, and an additional expression unit placed between the P and M genes containing the sequence of the domain III of the envelope E protein of the dengue 1 virus, FGA89 strain, fused to the apoptotic sequence of the Membrane M protein.

The vector may be cultivated in 100 μ/ml LB ampicillin medium after inoculating small colonies.

It is preserved long-term by freezing at −80° C.

The vector pTRE$_2$-SSCRT-ApoptoMden1/DIII-Hα1-2 was deposited at the CNCM (Paris, France) on 16$^{th}$ Jun. 2006 under number 1-3452.

This vector is a pTRE$_2$ plasmid containing the sequence of the signal peptide of human calreticulin fused to the pro-apoptotic sequences of the M protein and to the ectodomains III of the E protein with the α-helice sequences of the dengue 1 and 2 viruses.

The sequence of the insert contained in the plasmid and constituting a polynucleotide of the invention is SEQ ID NO: 9 shown in FIG. 8.

The vector may be cultivated in 100 g/ml LB ampicillin medium.

It is preserved long-term by freezing at −80° C.

The vector pTRE$_2$-ssCRT-ApoptoMden1/DIII-Hα3-4 was deposited at the CNCM (Paris, France) on 16$^{th}$ Jun. 2006 under number 1-3453.

This vector is a pTRE$_2$ plasmid containing the sequence of the signal peptide of human calreticulin fused to the pro-apoptotic sequences of the M protein of dengue 1 virus and to the sequences of the ectodomains III and Hα of the dengue 3-4 viruses.

The sequence of the insert contained in the plasmid and constituting a polynucleotide of the invention is SEQ ID NO: 11 shown in FIG. 9.

The vector may be cultivated in LB ampicillin 100 g/ml medium.

It is preserved long-term by freezing at −80° C.

The vector pTRE$_2$-ssCRT-ApoptoMden1/DIII-Hα1-2-3-4 was deposited at the CNCM (Paris, France) on 16$^{th}$ Jun. 2005 under number 1-3454.

This vector is a pTRE$_2$ plasmid containing the signal peptide sequence of human calreticulin fused to the pro-apoptotic sequences of the M protein of dengue 1 virus and to the sequences of the ectodomains III with α helices (Hα) of the E proteins of the dengue 1, 2, 3, 4 viruses.

The sequence of the insert contained in the plasmid and constituting a polynucleotide of the invention is SEQ ID NO: 4 shown in FIG. 2.

The vector may be cultivated in 100 μ/ml LB ampicillin medium.

It is preserved long-term by freezing at −80° C.

The vector pTRE$_2$-ssCRT-EctoM40den1/DIII-Hal-2-3-4 was deposited at the CNCM (Paris, France) on 16$^{th}$ Jun. 2005 under number 1-3455.

This vector is a pTRE$_2$ plasmid containing the signal peptide sequence of human calreticulin fused to the sequences of the ectodomain 1-40 of the M protein of the dengue 1 virus and to the sequences of the ectodomains III with α helices (Hα) of the E proteins of the dengue 1, 2, 3, 4 viruses.

The sequence of the insert contained in the plasmid and constituting a polynucleotide of the invention is SEQ ID NO: 17 shown in FIG. 12.

The vector may be cultivated in 100 g/ml LB ampicillin medium.

It is preserved long-term by freezing at −80° C.

The vector pUC57-TetraDVA (introduced into an *E. coli* strain) was deposited at the CNCM (Paris, France) on 14$^{th}$ Jun. 2006 under number 1-3619.

This vector is a pUC plasmid containing a nucleotide sequence optimized for the expression in mammalian cells of a tetrameric construct of the ectodomains III of the envelope E protein of the 4 serotypes (1, 2, 3, 4) of the dengue virus, fused to the ectodomain of the Membrane M protein.

Figure 25:
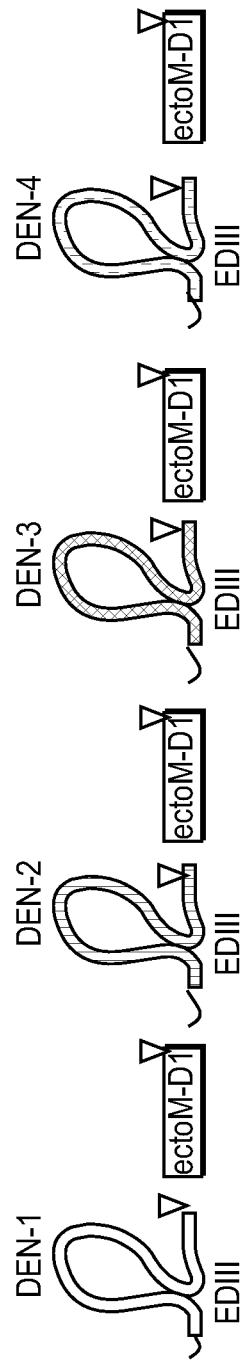

The insert contained in the plasmid vector is shown in FIG. 25.

The strain containing the vector may be cultivated in 100 g/ml LB ampicillin medium.

The vector pUC57-TetraDVB (introduced into an *E. coli* strain) was deposited at the CNCM (Paris, France) on 14$^{th}$ Jun. 2006 under number 1-3620.

This vector is a pUC plasmid containing a nucleotide sequence optimized for the expression in mammalian cells of a tetrameric construct of the ectodomains III of the envelope E protein of the 4 serotypes (1, 2, 3, 4) of the dengue virus, fused to the ectodomain of the Membrane M protein.

Figure 26:
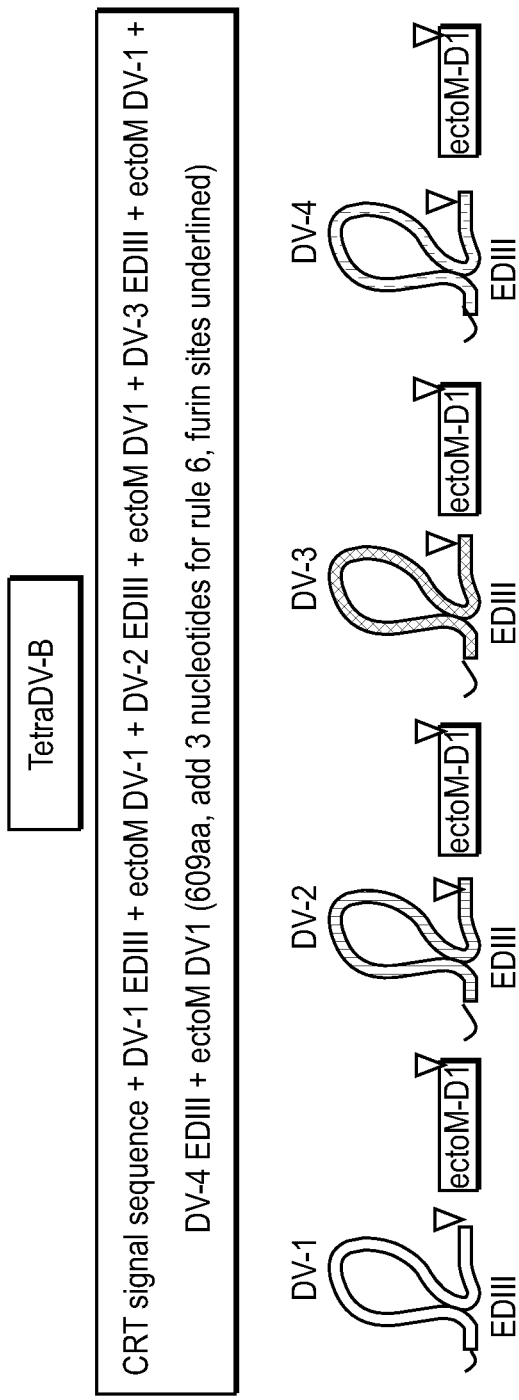

The insert contained in the plasmid vector is shown in FIG. 26.

The strain containing the vector may be cultivated in 100 μ/ml LB ampicillin medium.

The vector pUC57-TetraDVC (introduced into an *E. coli* strain) was deposited at the CNCM (Paris, France) on 14$^{th}$ Jun. 2006 under number 1-3621.

This vector is a pUC plasmid containing a nucleotide sequence optimized for the expression in mammalian cells of a tetrameric construct of the ectodomains III of the Envelope E protein of the 4 serotypes (1, 2, 3, 4) of the dengue virus, fused to the ectodomain of the Membrane M protein.

The insert contained in the plasmid vector is shown in FIG. 27.

The strain containing the vector may be cultivated in 100 μ/ml LB ampicillin medium.

The vector pUC57-TetraDVD (introduced into an *E. coli* strain) was deposited at the CNCM (Paris, France) on 14$^{th}$ Jun. 2006 under number 1-3622.

This vector is a pUC plasmid containing a nucleotide sequence optimized for the expression in mammalian cells of a tetrameric construct of the ectodomains III of the Envelope E protein of the 4 serotypes (1, 2, 3, 4) of the dengue virus, fused to the ectodomain of the Membrane M protein.

The insert contained in the plasmid vector is shown in FIG. 28.

The strain containing the vector may be cultivated in 100 μ/ml LB ampicillin medium.

The vector pUC57-TetraDVE (introduced into an *E. coli* strain) was deposited at the CNCM (Paris, France) on 14$^{th}$ Jun. 2006 under number 1-3623.

This vector is a pUC plasmid containing a nucleotide sequence optimized for the expression in mammalian cells of a tetrameric construct of the ectodomains III of the Envelope E protein of the 4 serotypes (1, 2, 3, 4) of the dengue virus, fused to the ectodomain of the Membrane M protein.

The insert contained in the plasmid vector is shown in FIG. 29.

The strain containing the vector may be cultivated in 100 μ/ml LB ampicillin medium.

3. Cloning and/or Expression Vectors and Antibodies

In a further aspect, the invention concerns any cloning and/or expression vector and any cell host (prokaryotic or eukaryotic) transformed by such a vector, and comprising regulation elements allowing the expression of the nucleotide sequence coding for a chimeric polypeptide of the invention. Such vectors are prepared using methods which are routinely used by the skilled person, and the resulting clones may be introduced into an appropriate host using standard methods such as, for example, lipofection, electroporation, thermal shock, transformation after chemical permeabilization of the membrane, or cell fusion.

The invention also encompasses host cells, in particular eukaryotic and prokaryotic cells, transformed by the vectors of the invention as well as transgenic animals, preferably mammals, with the exception of man, comprising one of said transformed cells of the invention. These animals may be used as models, to study the etiology of inflammatory and/or immune diseases, and in particular inflammatory diseases of the digestive tract, or in the study of cancers.

Of the cells which may be used in the present invention, the following may be cited: bacterial cells (Olins and Lee (1993), Curr Op Biotechnology 4: 520), but also yeast cells (Buckholz (1993), Curr Op Biotechnology 4, 538), as well as animal cells, in particular mammalian cell cultures (Edwards and Aruffo (1993), Curr Op Biotechnology 4, 558).

In the context of the present invention, the term "cloning and/or expression vector" refers to a polynucleotide construct designed to be transfected into different cell types. For this reason, these vectors encompass expression vectors designed for the expression of a nucleotide sequence in a host cell; cloning vectors designed for the isolation, propagation and replication of inserted nucleotides or shuttle vectors which comprise the attributes of more than one vector.

4. Polyclonal or Monoclonal Antibodies

The polypeptides and polynucleotides of the present invention may also be used to prepared polyclonal or monoclonal antibodies capable of binding (preferably in a specific manner) to at least one chimeric polypeptide/polynucleotide of the invention. The present invention thus also relates to such purified antibodies which may be obtained by very well known techniques such as, for example, the technique described by Kolher and Milstein (continuous cultures of fused cells secreting antibody of predefined specificity, Nature (1975), 262: 495-497). In a preferred embodiment of the invention, the antibodies are of the "humanized" type. A person skilled in the art would be able to use his general knowledge to prepare these types of antibodies.

5. Methods and Use

In a further aspect, the invention concerns the prevention and/or treatment of a Flaviviridae infection in a sensitive species. More particularly, the invention relates to the use of a recombinant viral vector of the invention for the preparation of an immunogenic composition intended for the prevention or treatment of a Flaviviridae infection in a sensitive species. The term "sensitive species" means any animal which is susceptible to a Flaviviridae infection, for example a human being.

The invention also relates to a method for preventing and/or treating a Flaviviridae infection in a sensitive species, comprising administering a pharmaceutically effective amount of at least one of the following elements:

- a chimeric polypeptide of the invention;
- a polynucleotide of the invention;
- a recombinant viral vector of the invention;
- an antibody of the invention; and
- a cloning and/or expression vector of the invention.

The term "Flaviviridae infection" means, for example, flaviviroses such as dengue, yellow fever, Japanese encephalitis and West Nile fever. The means for preparing and administering the elements of the present invention will not be described in more detail as they are already known to the skilled person.

6. Compositions

The present invention also concerns immunogenic compositions useful in the prevention and/or treatment of a Flaviviridae infection. The term "immunogenic composition" means a composition which contains elements having the capacity to induce, in vivo or in vitro, a cellular and/or humoral type immune response.

In a preferred embodiment, the composition of the present invention further contains a pharmaceutically acceptable vehicle and an element selected from the group constituted by:

- a polynucleotide of the invention;
- a chimeric polypeptide of the invention;
- a recombinant viral vector of the invention;
- an antibody of the invention; and
- a cloning and/or expression vector of the invention.

The compositions of the present invention may be in any solid or liquid form which is normal for pharmaceutical administration, examples of forms of administration being a liquid, a gel, or any other support which can allow controlled release, for example. Examples of compositions which may be used which may be cited are compositions which can be injected into human beings.

The compositions of the invention may also comprise components which increase or are capable of increasing the immunogenicity of the chimeric polypeptides of the invention, in particular other immunogenic peptides, specific or non-specific immunity adjuvants such as alun, QS21, Freund's adjuvant, $SBA_2$ adjuvant, montanide, polysaccharides or equivalent compounds.

A person versed in the art will be able to prepare pharmaceutically acceptable compositions and to determine, as a function of several factors, the preferred mode of administration and the amount which has to be administered. Factors which may influence the choice include: the nature of the treatment, the exact nature of the ingredients, active or non active, in the composition; the stage of the disease; the condition, age and weight of the patient, etc.

EXAMPLES

The following examples demonstrate other characteristics and advantages of the present invention and serve to illustrate rather than limit the scope of the present invention. Modifications and variations may be made without departing from the spirit and scope of the invention. Although other methods or products equivalent to those discussed below may be used to test or implement the present invention, preferred equipment and methods are described.

Example 1

The Recombined Measles virus $MV_{Schw}$-[EDIII+$M^{1-40}$]$_{DV-1}$ as a Prototype for a Candidate Vaccine Against Dengue (PTR156)

Figure 3:
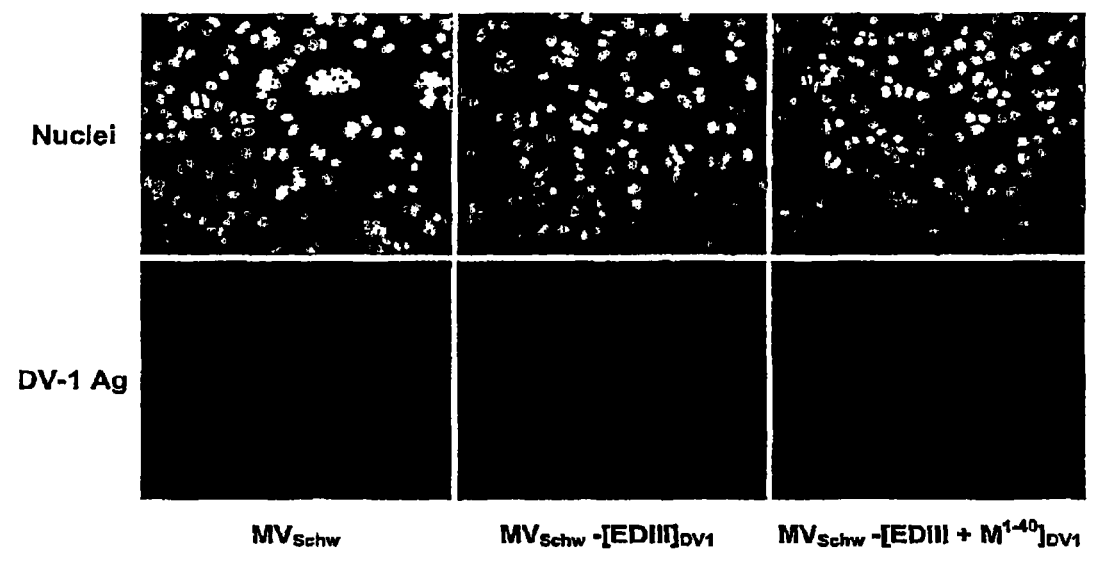
Figure 5:
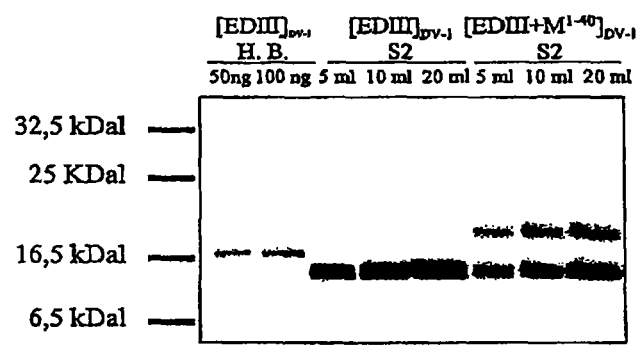
FIG. 5 shows the expression and secretion of the [EDIII]$_{DV-1}$ and [EDIII+M$^{1-40}$]$_{DV-1}$ antigenic domains in filtered and concentrated supernatants from *drosophila* S2 cells inducibly expressing these antigens.

Described in FIGS. 1 and 2, two immunogenic constructs based on the one hand on the capacity of domain III of the envelope E glycoprotein of the dengue virus to induce neutralizing antibodies and on the other hand on the involvement of the ectodomain of the membrane M protein ($M^{1-40}$) in viral pathogenicity (apoptosis) were inserted into the genome of the attenuated measles virus (Schwarz strain) (MVSchw). The viral sequences were under the dependency of the signal peptide of calreticulin to allow them to be targeted into the secretion pathway. The expression of the [EDIII]$_{DV-1}$ and [EDIII+$M^{1-40}$]$_{DV-1}$ sequences by the recombined viruses MVSchw was verified in infected Vero cells by indirect immunofluorescence using a polyclonal HMAF mouse serum directed against DV-1 (FIG. 3). Secretion of the EDIII and EDIII antigenic domains fused to the $M^{1-40}$ sequence (with the intercalating pentapeptide RRDKR) of the dengue virus, type-1 (DV-1) of the FGA/89 strain (Holmes E C et al, Mol Biol Evol 16(3): 405-409, 1999 and Desprès P et al, Virology 196: 209-219) was observed by Western blot analysis in the supernatants of cells infected with the $MV_{Schw}$-[EDIII]$_{DV-1}$ and $MV_{Schw}$-[EDIII+$M^{1-40}$]$_{DV-1}$ virus respectively (FIG. 4). Similarly, the production and secretion in the culture supernatants of a S2/[EDIII+$M^{1-40}$]$_{DV-1}$ drosophila cell line induced for expression of these proteins has been demonstrated (FIG. 5).

Two groups of four adult CD46/FNAR mice were immunized with 10 TCID50 of each of the recombined MVSchw viruses (Tables 1 and 2). The empty MVSchw virus was used as a negative control. We determined the production of antibodies directed against the MVSchw virus (MV Ag) and the DV-1 virus (DV-1 Ag) including those which were specific to EDIII (Thullier P et al, 2001, J Gen Virol 82: 1885-1892) and neutralizing (Anti-DV-1 FRNT75) in immunized mice (Tables 1 and 2). We observed that the $MV_{Schw}$-[EDIII]$_{DV-1}$ virus is less effective at producing specific antibodies to DV-1 or EDIII alone after two inoculations spaced by one month (Table 1). Using the same immunization protocol, we observed that the $MV_{Schw}$-[EDIII+$M^{1-40}$]$_{DV-1}$ virus induced significant titers of antibodies directed against DV-1 and against EDIII alone (Table 2). Anti-DV-1 antibodies including those which were neutralizing were still detected four months after the end of immunization.

When mice immunized more than 6 months previously with $MV_{Schw}$-[EDIII+$M^{1-40}$]$_{DV-1}$ were given a booster with a single dose of 5 μg of total proteins of a concentrate of supernatant of S2/[EDIII+$M^{1-40}$]$_{DV-1}$ drosophila cells induced for expression of the fusion protein [EDIII+$M^{1-40}$]$_{DV-1}$ and in the presence of Alugel as an adjuvant, large amounts of anti-DV-1, anti-EDIII and neutralizing DV-1 antibodies were observed, which means that there was a well established humoral memory response in the vaccinated animals (Table 2). The anti-DV-1 antibodies were still present several months after the antigenic booster (Table 2).

Three months after the antigenic booster with r[EDIII+$M^{1-40}$]$_{DV-1}$, mice immunized with $MV_{Schw}$-[EDIII+$M^{1-40}$]$_{DV-1}$ were inoculated intraperitoneally with $10^7$ FFU of FGA/NA did strain DV-1 (DV-1 is responsible for an asymptomatic infection in the IFNAR mouse). Large titers of anti-DV-1 antibody (in particular directed against EDIII) including those which neutralized DV-1 Hawaii strain (neutralizing titer #4000) were observed after 3 weeks of viral challenge (Table 2). It should be noted that mice immunized 9 months previously with $MV_{Schw}$-[EDIII+$M^{1-30}$]$_{DV-1}$ (this construct not inducing anti-EDIII antibody or neutralizing DV-1 antibody) then challenged intraperitoneally with $10^7$ FFU of FGA/NA did strain DV-1 produced anti-DV-1, anti-EDIII and neutralizing titers of 20000, 5000 and 80 respectively; these were values equivalent to those observed in BALB/c mice or IFNAR mice challenged under the same experimental conditions.

In conclusion, the fusion sequence [EDIII+$M^{1-40}$]$_{DV-1}$ secreted by the $MV_{Schw}$-[EDIII+$M^{1-40}$]$_{DV-1}$ virus is capable of generating neutralizing anti-DV-1 antibodies and of inducing a long term humoral memory response which is effectively stimulated on the one hand by the soluble antigen r[EDIII+$M^{1-40}$]$_{DV-1}$ and on the other hand in response to a viral infection. In contrast, the only antigenic EDIII domain secreted by the $MV_{Schw}$-[EDIII+$M^{1-40}$]$_{DV-1}$ virus is of low immunogenicity in CD46$^+$-FINAR mice. Our complementary work demonstrates that the pro-apoptotic ApoptoM ($M^{32-40}$) peptide at the C-terminal end of M determines the immunogenic power of the [EDIII+$^{M1-}$40]$_{DV-1}$ fusion sequence since the $MV_{Schw}$-[EDIII+$M^{1-30}$]$_{DV-1}$ virus without ApoptoM induces a production of anti-DV-1 antibody equivalent to that obtained after immunization with the $MV_{Schw}$-[EDIII]$_{DV-1}$ virus.

As a general methodology for pediatric vaccination against dengue, we propose to immunize young individuals with the $MV_{Schw}$-[EDIII+$M^{1-40}$]$_{DV-1}$ virus using a double inoculation spaced by one month, then to restimulate them later with the soluble r[EDIII+$M^{1-40}$]$_{DV-1}$ antigen as a vaccine booster or prophylactically against the risk of an infection by the dengue virus. This immunization strategy is being validated for the four serotypes of dengue based on an antigen composed of a tetramer of the four EDIII domains of DV-1, -2, -3 and -4 fused to the cytotoxic ApoptoM sequence.

Our first experimental results underline the importance of a reduced size immunogen derived from the envelope protein of the DV-1 virus in combination with the immunostimulating capacity of the live measles vector, a strategy which allows the induction of a neutralizing humoral response which is effective against the dengue virus. They define a proof of concept for the design of the tetrameric constructs of the antigenic domains of DV which will allow simultaneous and long term immunization against the four dengue serotypes.

Example 2

Construction of Chimeric Polypeptides Optimized for Expression in Mammals

In the present example, the inventors have developed novel antigenic constructs useful against a Flaviviridae infection.

These novel chimeric polypeptides are based on an antigen composed of a tetramer of the four EDIII domains of the four serotypes of the dengue virus, fused together and to one or the other of the cytotoxic apoptoM sequences shown in FIG. 30.

Thereafter, these chimeric polypeptides optimized for expression in a mammal were inserted into the genome of the attenuated measles virus, Schwarz strain, (MVSchw) viral strain. FIGS. 15 to 29 show the amino acid sequences of five preferred chimeric polypeptides and the polynucleotides encoding them.

These chimeric polypeptides were constructed using the following optimization conditions:

Optimization information for these sequences:
(Cai No=0.806, mean % GC=53.46, GC distribution: homogeneous about 50%);
elimination of internal "TATA box" sequences, a portion rich in AT or GC, elements with sequences ARE, INS and CRS, repeat sequences, sequences with secondary RNA structure, cryptic splicing sequences;
elimination of the following restriction sites: NheI, BamHI, XhoI, EcoRI, KpnI, SalI, BspEI, BglII, NotI, BssHII, BsiWI, with the exception of BsiWI in the first position and BssHII in the last position;
Elimination of TTTT, TTTAA, AAAGGG, AAAAGG, GGGAAA, GGGGAA motifs and their complements TTCCCC, TTTCCC, CCTTTT, CCCTTT.

TABLE 1

Antibody response directed against the MVSchw virus in CD46+/IFNAR mice inoculated i.p. with $MV_{Schw}$-[EDIII]$_{DV-1}$

| Immunization (month) | MV Ag titer[c] | DV-1 Ag titer[d] | DV-1 rEDIII titer[e] | Anti-DV-1 FRNT75[f] |
|---|---|---|---|---|
| 1[a] | 15000 | <100 | <100 | ND |
| 2[b] | 40000 | 100 | 10 | <10 |

[a]$10^4$ TCIP$_{50}$ of MV-DV-1 [EDIII + $M^{1-40}$]$_{DV1}$ was given i.p. to four adult mice;
[b]The individuals received a booster injection with $10^4$ TCIP$_{50}$ of MV-DV-1 [EDIII + $MV^{1-40}$]$_{DV-1}$;
[c]Determined by ELISA (Trinity Biotech) on pooled serums inactivated by heating;
[d]Determined by ELISA on pooled serums inactivated by heating. Microtitration plates were coated with $5 \times 10^5$ FFU of purified sucrose, FGA/NA d1d as viral antigen;
[e]Determined by ELISA on pooled serums inactivated by heating. Microtitration plates were coated with 50 ng of highly purified recombinant DV-1 EDIII as viral antigen;
[f]Anti-DV-1 neutralization antibodies were detected using a focus reduction neutralization test (FRNT). Pooled serums inactivated by heating were incubated with the DV-1 Hawaii line and titrating the virus on Vero cells using the plaque immunoassay test. FRNT75, the highest serum dilution tested, reduced the number of FFU by at least 75%.

TABLE 2

Antibody response directed against the MVSchw virus in CD46+/IFNAR mice inoculated i.p. with $MV_{Schw}$-[EDIII + $^{M1-}40$]$_{DV-1}$

| Immunization (months) | MV Ag titer[e] | DV-1 Ag titer[f] | DV-1 rEDIII titer[g] | Anti-DV-1 FRNT75[h] |
|---|---|---|---|---|
| 1[a] | 15000 | <100 | ≤100 | ND |
| 2[b] | 40000 | 1600 | 400 | 10 |
| 3 | 30000 | 1000 | 600 | 10 |
| 6 | 20000 | 500 | 100 | 40 |
| 7[c] | 20000 | 20000 | 100000 | 800 |
| 9 | 10000 | 2000 | 10000 | 100 |
| 10[d] | 10000 | 200000 | 800000 | 4000 |

[a]$10^4$ TCIP$_{50}$ of MV-DV-1 [EDIII + $M^{1-40}$]$_{DV1}$ was given i.p. to four adult mice;
[b]The individuals received a booster injection with $10^4$ TCIP$_{50}$ of MV-DV-1 [EDIII + $M^{1-40}$]$_{DV-1}$;
[c]The immunized mice received a booster injection of 5 μg of total secreted proteins deriving from a supernatant of S2 cells expressing rDV1 [EDIII + $M^{1-40}$]$_{DV-1}$ in the presence of Alugel adjuvant;
[d]The immunized mice were inoculated i.p. with $10^7$ FFU of FGA/NA d1d from the DV-1 line for three weeks;
[e]Determined by ELISA (Trinity Biotech) on pooled serums inactivated by heating;
[f]Determined by ELISA on pooled serums inactivated by heating. Microtitration plates were coated with $5 \times 10^5$ FFU of purified sucrose, FGA/NA d1d as viral antigen;
[g]Determined by ELISA on pooled serums inactivated by heating. Microtitration plates were coated with 50 ng of highly purified recombinant DV-1 EDIII as viral antigen;
[h]Anti-DV-1 neutralization antibodies were detected using FRNT. Pooled serums inactivated by heating were incubated with the DV-1 Hawaii line and titrating the virus on Vero cells using the plaque immunoassay test. FRNT75, the highest serum dilution tested, reduced the number of FFU by at least 75%.

The invention claimed is:

1. An isolated polynucleotide comprising a coding sequence that encodes a chimeric polypeptide, the chimeric polypeptide comprising at least one subdomain of an E protein of a dengue virus bound to at least one subdomain of a membrane M protein of a dengue virus, wherein the subdomain of the E protein comprises at least one ectodomain III peptide selected from amino acids 18 to 120 of SEQ ID NO: 20, amino acids 171 to 273 of SEQ ID NO: 20, amino acids 324 to 426 of SEQ ID NO: 20, and amino acids 477 to 579 of SEQ ID NO: 20, and wherein the subdomain of the membrane M protein comprises at least one peptide selected from amino acids 123 to 162 of SEQ ID NO: 3, amino acids 154 to 162 of SEQ ID NO: 3, and amino acids 122 to 132 of SEQ ID NO: 12.

2. The isolated polynucleotide of claim 1, wherein the encoded chimeric polypeptide comprises amino acids 18 to 624 of SEQ ID NO: 20.

3. The isolated polynucleotide of claim 1, wherein the encoded chimeric polypeptide comprises a dimer of ectodomain III peptides selected from amino acids 18 to 120 of SEQ ID NO: 20, amino acids 171 to 273 of SEQ ID NO: 20, amino acids 324 to 426 of SEQ ID NO: 20, and amino acids 477 to 579 of SEQ ID NO: 20.

4. The isolated polynucleotide of claim 1, wherein the encoded chimeric polypeptide comprises amino acids 18 to 120 of SEQ ID NO: 24.

5. The isolated polynucleotide of claim 1, wherein the subdomain of the M protein consists of amino acids 123 to 162 of SEQ ID NO: 3.

6. The isolated polynucleotide of claim 1, wherein the subdomain of the M protein consists of amino acids 154 to 162 of SEQ ID NO: 3 or amino acids 122 to 132 of SEQ ID NO: 12 which is an apoptoM sequence.

7. The isolated polynucleotide of claim 1, wherein the encoded chimeric polypeptide further comprises a binding segment binding the subdomain of the E protein to the subdomain of the M protein.

8. The isolated polynucleotide of claim 7, wherein the binding segment is a pentapeptide having the amino acid sequence RRDKR (SEQ ID NO: 34) or RREKR (SEQ ID NO: 35).

9. A recombinant attenuated measles viral vector comprising the polynucleotide according to claim 1 inserted into the viral genome.

10. The recombinant measles viral vector of claim 9, wherein the vector is a live measles or Schwarz strain viral vector.

11. A recombinant measles viral vector selected from the measles viral vectors deposited at the COLLECTION NATIONALE DE CULTURES DE MICROORGANISMES (CNCM) (Paris, France) under numbers I-3440, I-3442, I-3452, I-3453, I-3454, I-3455, I-3619, I-3620, I-3621, I-3622 and I-3623.

12. A cloning or expression vector comprising the polynucleotide as defined in claim 1.

13. An immunogenic composition comprising the recombinant measles viral vector according to claim 9 and a pharmaceutically acceptable vehicle.

14. A method for treating a dengue infection in a sensitive species, comprising: administering a pharmaceutically effective amount of an immunogenic composition according to claim 13 to the sensitive species.

15. The method according to claim 14, further comprising administering a second pharmaceutically effective amount of the immunogenic composition as a booster immunization.

* * * * *